United States Patent
Miar et al.

(10) Patent No.: US 11,433,423 B2
(45) Date of Patent: Sep. 6, 2022

(54) ELECTROACTIVE MATERIALS COMPRISING A PIEZOELECTRIC POLYMER AND A CONDUCTING POLYMER

(71) Applicants: Solaleh Miar, San Antonio, TX (US); Teja Guda, San Antonio, TX (US); Anson Joo Leng Ong, San Antonio, TX (US)

(72) Inventors: Solaleh Miar, San Antonio, TX (US); Teja Guda, San Antonio, TX (US); Anson Joo Leng Ong, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 221 days.

(21) Appl. No.: 16/221,972

(22) Filed: Dec. 17, 2018

(65) Prior Publication Data

US 2020/0023408 A1 Jan. 23, 2020

Related U.S. Application Data

(60) Provisional application No. 62/599,614, filed on Dec. 15, 2017.

(51) Int. Cl.
| | | |
|---|---|---|
| *B05D 5/12* | (2006.01) | |
| *C08L 27/16* | (2006.01) | |
| *C08L 39/04* | (2006.01) | |
| *B05D 3/14* | (2006.01) | |
| *A61L 27/16* | (2006.01) | |
| *A61L 27/34* | (2006.01) | |
| *B05D 7/24* | (2006.01) | |
| *A61L 27/54* | (2006.01) | |
| *H01L 41/193* | (2006.01) | |

(52) U.S. Cl.
CPC ............... *B05D 5/12* (2013.01); *A61L 27/16* (2013.01); *A61L 27/34* (2013.01); *A61L 27/54* (2013.01); *B05D 3/145* (2013.01); *B05D 7/24* (2013.01); *C08L 27/16* (2013.01); *C08L 39/04* (2013.01); *A61L 2300/414* (2013.01); *B05D 2201/02* (2013.01); *B05D 2256/00* (2013.01); *B05D 2451/00* (2013.01); *B05D 2518/00* (2013.01); *H01L 41/193* (2013.01)

(58) Field of Classification Search
None
See application file for complete search history.

(56) References Cited

U.S. PATENT DOCUMENTS

| | | | |
|---|---|---|---|
| 9,078,805 B2 | 7/2015 | Mueller | |
| 9,155,861 B2 | 10/2015 | Hetke | |

FOREIGN PATENT DOCUMENTS

| | | |
|---|---|---|
| JP | 5714814 B2 | 12/2009 |
| KR | 101261469 | 4/2011 |

OTHER PUBLICATIONS

Dias et al., "Electrical properties of intrinsically conductive core-shell polypyrrole/poly(vinylidene fluoride) electrospun fibers", Synthetic Metals 197, 2014, pp. 198-203.*
George et al., "Electrically Controlled Drug Delivery from Biotin-Doped Conductive Polypyrrole", Adv. Mater. 2006, 18, pp. 577-581.*
Lee, et al., "Polypyrrole-coated electrospun PLGA nanofibers for neural tissue applications", NIH, Biomaterials, Sep. 2009; 30(26).
George, et al. "Electrically Controlled Drug Delivery from Biotin-Doped Conductive Polypyrrole", Advanced materials 2006, 18.
Miar, et al., "Electrical Stimulation Based Controlled Drug Delivery from Polypyrrole coated Polyvinylidene fluoride " UT Health Science Center, Nov. 2016.
Miar, Solaleh "Development Of El Fctroactive Materials as Substrates for Drug Delivery", thesis defended Aug. 2016.

* cited by examiner

*Primary Examiner* — Robert A Wax
*Assistant Examiner* — Randeep Singh
(74) *Attorney, Agent, or Firm* — Thomas | Horstemeyer, LLP

(57) ABSTRACT

In one embodiment, an electroactive material includes a piezoelectric polymer substrate and a conducting polymer coating provided on the substrate.

12 Claims, 13 Drawing Sheets

ELECTROACTIVE MATERIALS COMPRISING A PIEZOELECTRIC POLYMER AND A CONDUCTING POLYMER

CROSS-REFERENCE TO RELATED APPLICATION

This application claims priority to U.S. Provisional Application Ser. No. 62/599,614, filed Dec. 15, 2017, which is hereby incorporated by reference herein in its entirety.

BACKGROUND

There has been increased interest in electroactive materials for various biomedical applications including biosensors, scaffolds for tissue regeneration, and drug delivery carriers. It would be desirable to have further electroactive materials for use in such applications.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have electroactive materials for use in biomedical applications, such as biosensors, scaffolds for tissue regeneration, and drug delivery carriers. Disclosed herein are examples of such electroactive materials. In some embodiments, the electroactive materials comprise polymeric materials that include both a piezoelectric polymer and a conducting polymer. By way of example, the electroactive materials can comprise a piezoelectric polymer that is coated with a conducting polymer using an electrochemical polymerization process. When a therapeutic substance, such as a drug, is loaded into the conducting polymer, the conducting polymer will release the substance into surrounding tissue in which the electroactive material is provided when an electrical potential is applied to the electroactive material. In addition, the piezoelectric polymer will contract and/or expand in response to the applied electrical potential and this contraction/expansion is transmitted to the tissue to enhance the therapeutic effect. Accordingly, a synergistic effect is achieved through the use of the two different types of polymers. Although such electroactive materials are useful in such biomedical applications, it is noted that other applications are possible as, generally speaking, the electroactive materials have the capability to transform energy between three different forms: mechanical, electrical, and chemical.

In the following disclosure, various specific embodiments are described. It is to be understood that those embodiments are example implementations of the disclosed inventions and that alternative embodiments are possible. All such embodiments are intended to fall within the scope of this disclosure.

Piezoelectric Polymers

Piezoelectricity has been demonstrated in some biologic tissues, including bone and extracellular matrix proteins, such as collagen. Synthetic piezoelectric materials can mimic biophysical interactions in the body and potentially generate better regenerative outcomes in tissue engineering. Among the available piezoelectric materials, polymers show the most promise for such applications, owing to a wide range of tunable mechanical and chemical properties, low costs of production, and relatively easy processing methods. For biomedical applications in particular, there are several biocompatible piezoelectric polymers, including polyamide, poly(vinylidene fluoride) (PVDF), poly(lactic acid), and polyhydroxybutyrate.

Figure 1:
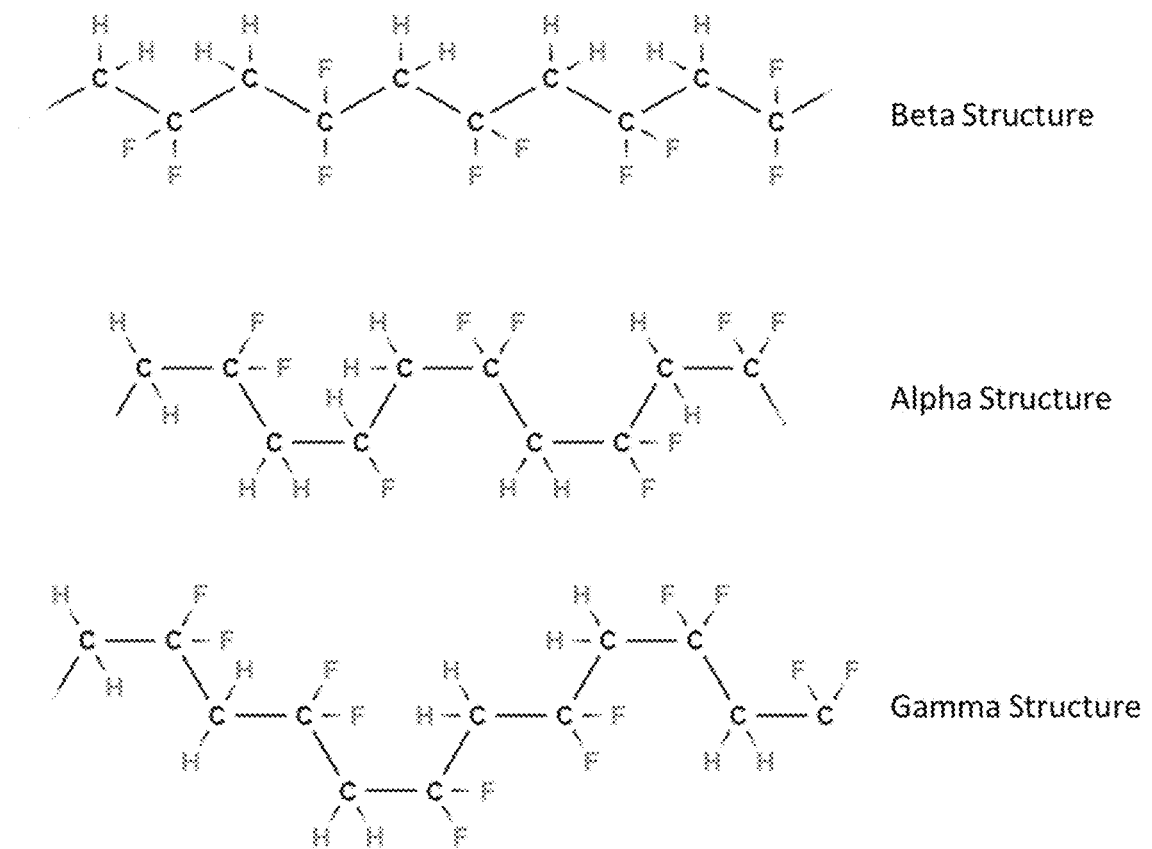
FIG. 1 is a diagram that shows three of the four crystal structures of poly(vinylidene fluoride) (PVDF). The beta (β) structure (of greatest interest for piezoelectricity), the alpha (α) structure (of least interest for piezoelectricity), and the gamma (γ) structure are shown.

Among the available biocompatible polymers, polyvinyledene fluoride (PVDF) has the strongest piezoelectric properties. The remarkable polymorphism exhibited by PVDF is manifested as four different crystalline phases, including alpha ($\alpha$), beta ($\beta$), gamma ($\gamma$), and delta ($\delta$). Of these, the $\beta$ phase exhibits the highest piezoelectricity and is consequently the most desirable phase for tissue regeneration. On the other hand, the $\alpha$ phase is a nonpolar phase with the lowest piezoelectric properties. FIG. 1 shows the different polymorphisms of PVDF. There are various techniques available in order to increase the $\beta$ phase of a piezoelectric polymer during the fabrication process, such as annealing, uniaxial stretching, and electrospinning. In addition to the relative fraction of the $\beta$ phase in the PVDF (referred to as the $\beta$ ratio), the alignment of $\beta$ phases is also essential since the direction of $\beta$ phase directly affects the piezoelectric response. Consequently, if applied electromechanical stimulations are aligned with the direction of $\beta$ phases in PVDF fibers, the strongest piezoelectric response can be achieved. The methods available to increase the alignment of $\beta$ phases include uniaxial stretching methods, corona discharge, and electrospinning. It has been demonstrated that the uniaxial stretching method helps align $\beta$ phase perpendicular to the tensile direction. Although this method is practical, it may not be optimal for tissue regeneration applications of PVDF since it is dependent on fiber morphology. Another method is corona discharge, which causes poling of the PVDF under high electric fields (0.5 to 2.5 MV/cm). This method is limited to thin samples and the direction of the poling state is aligned with the direction of the electric field.

Electrospinning is a versatile method to provide cells an appropriate environment for better expansion, proliferation, and alignment. These advantages are due to an increase in surface area and modification of the scaffold's morphology. It has been hypothesized that, since the fibers are reasonably elastic and mimic the structure of the native extracellular matrix, cells are also able to deform the fibers to enable migration and proliferation into the electrospun mats. Moreover, muscle and nerve cells grow aligned on aligned electrospun mats, which is favorable for functional tissue regeneration. In electrospinning, the high voltage applied to the polymer polarizes the PVDF solution while fibers are drawn. The $\beta$ ratio achieved via conventional electrospinning could be as high as 95%, with a poling direction perpendicular to the longitudinal axis of the fibers, and the electrospun PVDF fibers exhibit piezoelectric properties under compressive stresses. All these factors suggest that electrospinning is a promising technique for the manufacture of PVDF based fibrous substrates for tissue engineering applications.

Conducting Polymers

Many body tissues are highly sensitive to electric stimuli and the application of an electric field can trigger them to significantly alter cell growth, differentiation, and/or migration. In the field of bone and neuromuscular tissue engineering, the underlying cells respond strongly to appropriate electrical stimulation. One of the critical elements necessary to harness this phenomenon is the conductivity of the micro-environment, and specifically scaffolds, which enables the applied electrical stimulus to be effectively transmitted to the cells. Various synthetic polymers have demonstrated both acceptable biocompatibility and sufficient conductivity for use in biomedical applications, including polypyrrole (PPy), polyaniline, and polythiophene.

Figure 2:
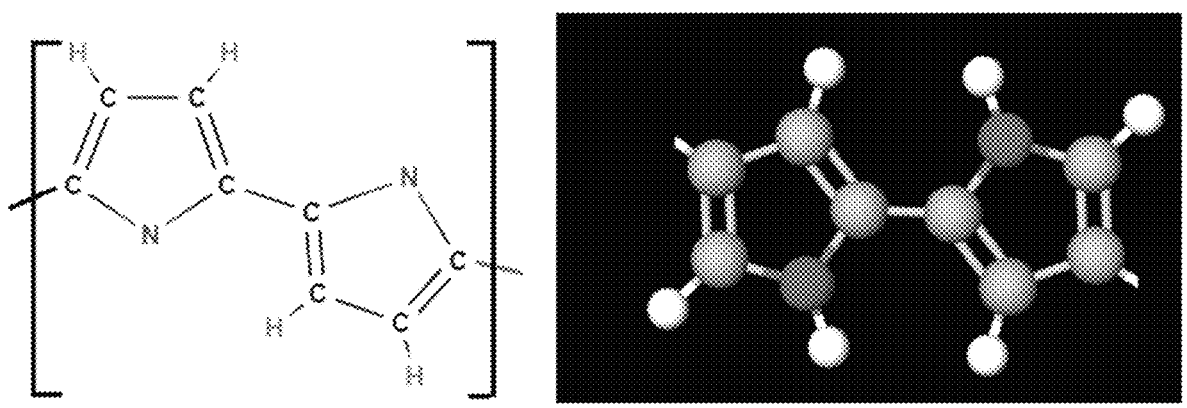
FIG. 2 is a diagram that shows the chemical structure of polypyrrole (PPy).

PPy is one conducting polymer that has numerous applications in tissue engineering and drug delivery systems. Ease of synthesis, inherent conductivity, stability in aqueous environments, and biocompatibility have made this polymer a promising drug/growth factor carrier or cell guidance candidate for tissue engineering applications. These properties are mostly the same for polyaniline and polythiophene as well. PPy is made from pyrrole, which is a polyheterocycle, and PPy polymerization occurs upon oxidation of pyrrole, which leads to the formation of a conjugated chain (FIG. 2). Positive charge in the backbone and overlapping of the $\pi$ electrons results in a high electrical capacity and conductivity in PPy. PPy is a neutral amorphous polymer and PPy film obtained through different polymerization techniques is a rigid film due to the presence of doping agents. Moreover, the polymer produced after polymerization is a dark (blue to black), insoluble but swellable film.

One of the most important properties of PPy and other conducting polymers is the redox property, which is the ability of the polymer network to convert from a conductive to an insulating state. The insulating state is a neutral or reduced state, but the oxidized state is the network with lack of electrons in the polymer backbone. In order to produce a conductive network, doping agents are required as they dope the polymer with a negative charge. Delocalization of electrons in the polymer backbone not only brings properties such as conductivity but also photosensitivity. In terms of polymerization methods, PPy is prepared by the oxidation of commercial pyrrole monomers through chemical or electrochemical polymerization. Chemical or oxidative polymerization includes high oxidation of pyrrole monomer and chain growth during the propagation step until the termination step while exposed to strong oxidizing agents such as ferric chloride, ammonium persulfate, ferric perchlorate, and ferric p-toluenesulphonic acid.

Another method used to produce a thin layers of PPy is vapor polymerization in which the monomer solution is sprayed on a surface that has been pre-coated with an oxidizing agent. In oxidative polymerization, the key point is the formation of long chain oligomers or small chain PPy that is soluble enough to polymerize further. Therefore, one of the advantages of chemical polymerization is the wide range of usable oxidizing agents and polymerization in a desirable site of reaction. On the other hand, a limitation of chemical polymerization of PPy is that the polymer results in a porous bulk polymer with poor mechanical properties or manifests as particles.

Electrochemical polymerization is an alternative method that, while more complicated than chemical polymerization, generally offers superior conductivity and mechanical properties. This method has different techniques including galvanostatic, potentiostatic, and potentiodynamic polymerization. In all the methods, polished platinum, gold or glassy carbon electrodes, stainless steel sheets, and Ag/AgCl-saturated calomel or reference electrodes are used in a one-compartment cell as the counter, the working, and the reference electrodes, respectively. Monomer oxidation occurs on the working electrode through electrodeposition produced by the current passed through the solution. The reference electrode measures the voltage at the working electrode and balances the potential, while the counter electrode generates a balance current through the polymerization solution. The polymerization solution contains the pyrrole monomer, doping agent, and solvents. The produced PPY film is attached to the electrode.

Under potentiostatic conditions, the current may change versus time but the voltage is constant. The voltage should be optimized carefully for this process since high voltage causes high oxidation and results in polymer degradation. In the galvanostatic method, the current is held constant and the polymerized film is in an oxidized conductive state to avoid poor polymerization and the production of a resultantly thinner film.

Galvanostatic polymerization leads to a thicker film in comparison to the potentiostatic method since the thickness of the deposited polymer depends on the duration. Under potentiostatic conditions, polymerization cessation typically occurs in thick films but an increase in potential occurs in the galvanostatic method due to current control. Potentiodynamic polymerization or the cyclic voltammetry method requires a potential waveform that changes with time. In galvanostatic and potentiostatic polymerization, the polymer is in a highly oxidative state, while in the potentiodynamic polymerization it undergoes periodic oxidation.

In all electrochemical methods, there are many parameters that affect the properties of the resulting PPy film, including temperature, pH, solvents, nature of electrodes, applied current, and potential. Generally speaking, working electrodes are polished and washed with ethanol before the polymerization because the reaction at the working electrode can compete with the oxidation of monomers. The electrolyte concentration and doping agent used also affect nucleation, polymer growth, and conductivity. Moreover, the solvent used for the polymerization solution should have good conductivity and electrochemical resistance.

Furthermore, temperature affects mechanical, redox properties, and conductivity such that, as the temperature increases, the rate of polymerization also increases but results in a decrease in conductivity and redox properties. The pH of the environment also plays a critical role, with neutral or weakly acidic electrolytes increasing polymerization efficiency. This is due to the increase in cation radicals that prevent radical-radical coupling. In addition, the increase in current and potential decrease the ultimate tensile strength inversely and PPy doped with high doping agent concentrations exhibits higher tensile strength. Doping agents also contribute to polymer stability in various environments.

During last two decades, conducting polymer scaffolds have been designed for applications in neural, neuromuscular, bone, and cardiac tissue engineering due to the favorable properties of these polymers, including biocompatibility, biodegradability, and the ability to release biological agents in a controllable manner via electrical impulses. The combination of conducting polymers such as PPy with hyaluronic acid exhibited improved vascularization in vivo appropriate for bone and neural tissue engineering. The survival rate and proliferation of Schwann cells on PPy was investigated and it was observed that PPy demonstrated good biocompatibility with rat peripheral nerve tissue. As previously mentioned, poly(D,L-lactic acid) modifies PPy's electrochemical properties and this has led to a significant increase in neurite length under electrical stimulation. There have been similar results when using PPy doped with a nerve growth factor, which demonstrated a 50% higher neurite growth under electrical stimulation. Although the electrical stimulation for bone regeneration has been studied, the impact of conducting polymers in tissue engineering has been greatest in neural tissue engineering. Among conducting polymers, PPy shows superior induction of mesenchymal stem cell (MSC) osteogenicity.

Conducting polymers in general, and PPy in particular, show remarkable potential as promising carriers for controllable drug delivery. For this application, the delocalization of charges through electrical stimulation helps the encapsulated biological agents to be released from the conducting polymers. Burst release may occur in these systems, which may be beneficial or deleterious to the specific application. Some of the limitations in drug loading are passive leakage, low drug loading within the structure, poor controlled release of biological agents with large molecular weights, and the fatigue of conducting polymers subjected to cycles of electrical stimulation. A novel solution to some of these problems is the recently reported polymerization of PPy with biotin used as the doping agent, which could be bound first to streptavidin and further to a protein payload for controlled delivery of the conjugate. In summary, conducting polymers can be used for controlled drug delivery application under electrical stimulus.

Piezoelectric Polymer and Conducing Polymer Synergy

Biophysical stimulations have been used to improve cellular functions, such as morphology, migration, and gene expression for tissue engineering applications, such as in vitro skeletal muscle regeneration. It has been shown that mechanical stimulation, such as repetitive stretch/relaxation of skeletal muscle cultures, improves structural organization including cell orientation. Additionally, skeletal myoblasts have also been shown to respond to electrical stimulation. A novel possibility for internally applying electrical signals to substrates for the regeneration of biological tissues is possible by using biocompatible piezoelectric polymers such as PVDF. PVDF has the highest piezoelectric properties among various biocompatible, piezoelectric polymers, implying that applied electrical signals would be converted into mechanical stimulation and transmitted to cells in a potentially direct and synergistic manner. However, the hydrophobicity and low conductivity of PVDF are some shortcomings, which needed to be modified for the material to be suitable for translational therapeutic applications. One of possible solution to these shortcomings is the use of a secondary, biocompatible, conducting polymer, such as PPy. PPy not only has improved hydrophilicity, but also might be considered as a biochemical drug depot for targeted and controlled drug release. One method for the polymerization of PPy is to use electrochemical deposition, which limits its applications because PPy then attaches only to the working electrode.

Disclosed herein is a modified in situ polymerization technique that provides a conducting polymer coating on a piezoelectric polymer substrate. In studies described in the sections that follow, PPy was used as the conducing polymer, PVDF was used as the piezoelctric polymer, and basic fibroblast growth factor (bFGF) was used as a model drug. In the studies it was hypothesized that PPy will be induced to release the bFGF when electrically stimulated, while the substrate PVDF will provide a simultaneous mechanical response. In the studies, the goal was to achieve a composite scaffold substrate based on PVDF-PPy, which releases growth factor with retained bioactivity and provides biophysical stimulation simultaneously upon applied electrical stimulation for potential use in biomedical and regenerative medicine applications.

Production of Electroactive Materials Comprising Piezoelectric and Conducting Polymers Electroactive materials comprising piezoelectric and conducting polymers were first produced. As part of this process, pyrrole (98%), PVDF (Mw: 275,000), sodium p-toluenesulfonate (PTS)(95%), iron(III) chloride, biotin, N,N dimethylformamid (DMF), and acetone were purchased from Sigma-Aldrich (St. Louis, Mo.). Unmodified bFGF and CellTiter-Gb® were obtained from Promega (Madison, Wis.). HRP-streptavidin conjugated, biotinylated bFGF, human fibroblast growth factor (FGF) Basic DuoSet ELISA Development kit, and BALB/3T3 clone A31 were supplied from Thermo Fisher (Austin, Tex.), Acro Biosystems (Newark, Del.), R&D Systems (Minneapolis, Minn.), and ATCC (Manassas, Va.), respectively. Pyrrole was distilled under nitrogen gas and stored in −20° C. and iron (III) chloride was used without any purification.

The PVDF was dissolved in DMF/acetone and was then loaded into an automated syringe pump. An 18-gauge needle was used for all the studies. A rotator covered with aluminum foil was used as the collector and was located at a fixed traveling distance from the syringe tip. High voltage was applied to the polymer solution and fibers were drawn due to the high electric field established. The electrospinning setup and process parameters, such as voltage (10-30 kV), traveling distance (15-30 cm), flow rate (0.005-0.1 ml/min), rotating speed (2, 4, and 6), and size of the drum (radius: 1-2.5 cm) were varied to ascertain optimized process parameters for the generation of electrospun fibers (Table 1). The criteria used for optimization was to produce fibers with the greatest alignment, with the least defects (such as beads) and with the best piezoelectric properties as quantified by the β ratio. At least three independent experimental replicates were produced for the characterization of the fibers.

TABLE 1

List of settings under which PVDF fibers were generated to evaluate the effect of process parameters on resultant fibers using a one-factor-at-a-time design of experiment.

| Sample Label | Traveling Distance (cm) | Rotating speed (rpm) | Voltage (KV) | Solvent (w:w) | Flow rate (ml/min) | Drum size (radius: cm) |
|---|---|---|---|---|---|---|
| TD10 | 10 | 1410 | 20 | 3:2 | 0.01 | 2.5 |
| TD20 | 30 | 1410 | 20 | 3:2 | 0.01 | 2.5 |
| RS4 | 30 | 940 | 20 | 3:2 | 0.01 | 2.5 |
| RS2 | 30 | 470 | 20 | 3:2 | 0.01 | 2.5 |
| V10 | 30 | 1410 | 10 | 3:2 | 0.01 | 2.5 |
| V30 | 30 | 1410 | 30 | 3:2 | 0.01 | 2.5 |
| S DMF | 30 | 1410 | 20 | Only DMF | 0.01 | 2.5 |
| S 4:1 | 30 | 1410 | 20 | 4:1 | 0.01 | 2.5 |
| FR 0.005 | 30 | 1410 | 20 | 3:2 | 0.005 | 2.5 |
| FR 0.1 | 30 | 1410 | 20 | 3:2 | 0.1 | 2.5 |
| DS 1 | 30 | 1410 | 20 | 3:2 | 0.01 | 1 |
| DS 2.5 | 30 | 1410 | 20 | 3:2 | 0.01 | 2.5 |

Pyrrole monomer (Sigma, St. Louis, Mo.) was distilled prior to polymerization to remove inhibitors. After distillation, in situ polymerization of PPy was performed at low temperature (4° C.) and in the presence of FeCl$_3$ (Sigma, St. Louis, Mo.) as the initiator initiated the reaction at room temperature upon adding it to the polymerization solution. Biotin was utilized as the co-dopant in the polymerization for further growth factor loading. For this purpose, the polymerization solution was saturated with biotin (Sigma, St. Louis, Mo.) dissolved in ethanol to increase the cooperation of biotin in the polymerization. On the other hand, the ratio of main dopant, which was sodium p-toluenesulfate (Sigma, St. Louis, Mo.), was ten times less than the regular amount to assist the cooperation of biotin.

PVDF fibers were cut into mats 1×1 cm in size and were incubated in the polymerization solution for 30 minutes with gentle shaking. The polymerization solution contained 0.014 mol (~1 ml) polypyrrole, 0.0014 mol (0.272 gm) sodium p-toluenesulfate, and 0.047 mmol (14.35 ml saturated in ethanol) biotin in 2 ml of deionized (DI) water. Then, the initiator was added to the polymerization solution (0.0042 mol-0.684 gm FeCl$_3$ in 2 ml deionized water). Samples were incubated at 4° C. In addition, a separate sample was polymerized without biotin (14.35 ml of pure ethanol without biotin instead of the saturated biotin solution). The reaction was stopped after 1, 6, 12, 18, and 24 hours in order to evaluate the impact of polymerization duration on polymerization. Next, the coated samples were washed for 3 days with copious amount of deionized water and ethanol (30:70 w/v) to remove any polymerization debris and unreacted chemicals. Coated samples were further evaluated by scanning electron microscopy (SEM) and attenuated total reflectance-Fourier transform infrared spectroscopy (ATR-FTIR), and using the Sessile Drop technique to characterize the coating and the contribution of biotin to the polymerization.

Evaluation of the Electroactive Polymer Fibers

SEM was used to characterize the morphology of the electrospun fibers. PVDF samples-after electrospinning were kept in a vacuum chamber to remove all solvents. Three samples were collected per group both before and after the PPy coating, and further coated with silver using a sputter coater. The samples were then imaged using an applied voltage of 20 kV at magnification factors of 500, 1000, and 2000.

The piezoelectric efficiency of PVDF can be evaluated through by its β ratio, which is the relative fraction of the β phase in the polymer and can be measured quantitatively through ATR-FTIR. Infrared absorption bands at 530 and 840 from a Tensor 27 ATR-FTIR (Bruker Optics, Billerica, Mass.) results were used as the characteristics of α and β phases, respectively. Infrared absorption at relative fraction of β phase was calculated using the β ratio equation:

$$f(\beta) = \frac{A_\beta}{1.26 A_\alpha + A_\beta} \times 100 \quad \text{(Equation 1)}$$

where $A_\beta$ and $A_\alpha$ are related absorbance for β and α ratio, respectively.

The contact angle between water and electrospun mats either as prepared or coated with PPy was measured using the sessile drop technique (VCA Optima, Billerica, Mass.) at room temperature. A water droplet was introduced on the flat surface of mats and the angle was recorded using software provided with the contact angle machine.

PPy coated PVDF samples were hydrated with different ethanol-sterile DI water solutions (50:50, 30:70, 10:90, 0:100). Then, they were incubated in unmodified streptavidin-horse radish peroxidase solution 1 ml diluted in 5 ml phosphate-buffered saline (PBS) for 15 minutes at 4° C. and washed three times with PBS to remove non-conjugated streptavidin. Then 18 μg biotinylated bFGF (0.001 μmol) was added to the sample, incubated for 30 minutes, and again washed three times with PBS. Then, samples were kept in fresh serum-free media for further drug release studies.

Tissue culture plates were equipped with platinum wires in a custom setup for electrical stimulation. Samples were incubated in the bioreactor containing serum-free media and media was collected to identify passive drug leakage without stimulation. Subsequently, the electric pulses (5 V/cm) were applied to the samples for 1, 2, 5, 10, 30 minutes and finally an hour. Media was collected and fresh media replenished to the sample well each time. Then, samples were retained in the solution for 5 minutes. Finally, collected supernatant was stored at −4° C. for ELISA quantification (George, LaVan et al. 2006) and assessment of bioactivity. The Human FGF Basic DuoSet ELISA Development kit was utilized in order to quantify the presence of bFGF.

The biological activity of the released biotinylated bFGF was evaluated with a CellTiter-Glo (Promega, Madison, Mich.) cell viability assay by testing the ability to stimulate the proliferation of BALB/3T3 clone A31 cell line. This protocol has been established by Promega as the assay to determine the bioactivity of rhFGF, basic, with BALB/C 3T3 fibroblasts. Briefly, a cell suspension containing 5000 cells/per well was used for each well (96-well plate) and cells were grown in the media containing 5 ng/ml of the supernatant containing biotinylated bFGF (Acro Biosystems, Newark, Del.), unmodified bFGF (Promega, Madison, Mich.), biotinylated bFGF collected under stimulation, and no bFGF (negative controls). The absorbance was recorded at 490 nm using an ELISA plate reader.

Six samples after polymerization and growth factor loading were kept for two months to test the stability of coating and the longer term release of growth factor, as well as shelf life stability. SEM was used to qualitatively evaluate the morphology of the coated fibers, while the drug release studies will be analyzed for statistical significance using one-way analysis of variance (ANOVA) followed by Tukey's test for post hoc determination of significant differences at $p<0.05$.

Results

Post-fabrication, PVDF fibers were maintained in a vacuum for 24 hours to remove all solvents and then the fibers were analyzed via SEM. The SEM results clearly exhibit the impact of electrospinning parameters on the morphology of the fibers.

Figure 3:
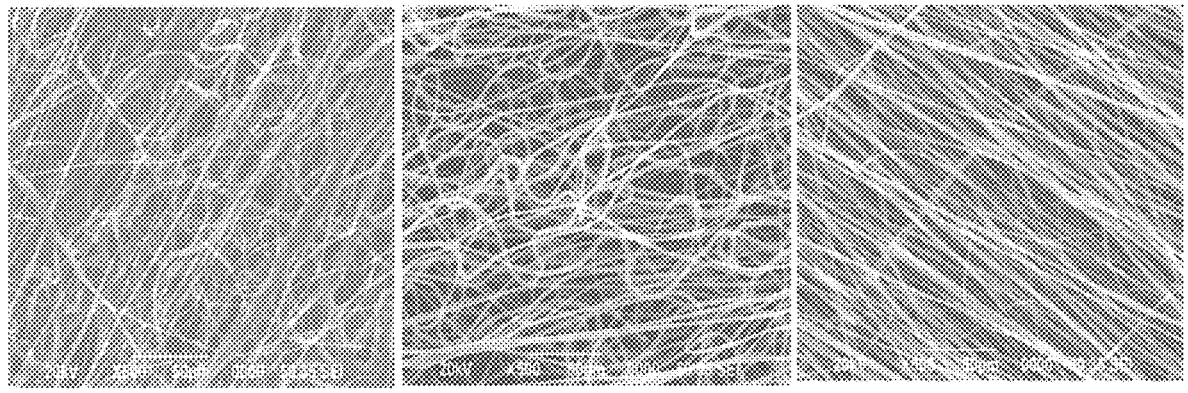
FIG. 3 includes scanning electron microscope (SEM) images that illustrate the impact of traveling distance on the PVDF fiber morphology (TD10, TD20, TD30 from left to right).
Figure 4:
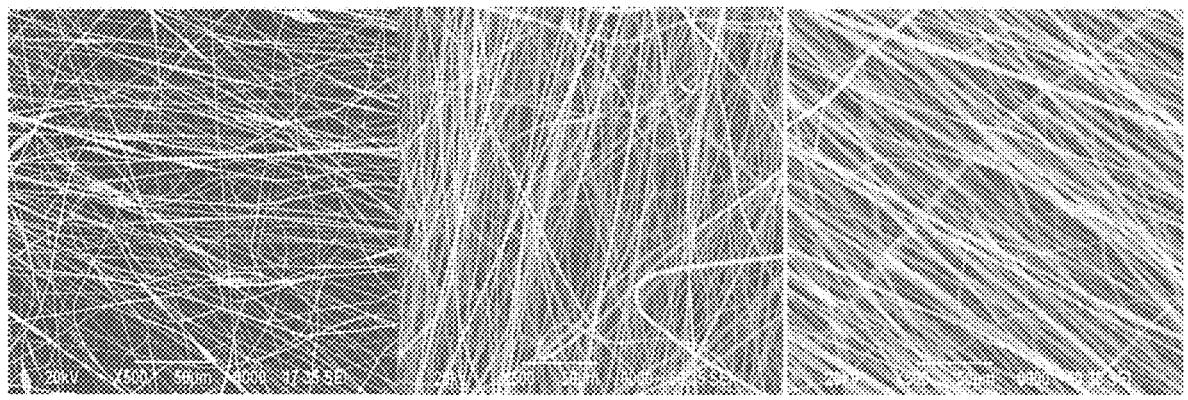
FIG. 4 includes SEM images that illustrate the impact of collector rotation speed on the PVDF fiber morphology (470 rpm, 940 rpm, 1410 rpm from left to right).

In the sample TD10, drawn fibers were not consistent and in TD20, although the fibers are consistent, they were relatively poorly aligned. When the traveling distance increased to 30 cm, fibers became more aligned while maintaining their consistency (FIG. 3). In terms of the rotating speeds of the collector drum, low speed, such as 470 rpm, was not able to align the fibers. As the rotating speed was increased the alignment of the fibers was increased as well, as observed at 940 rpm (FIG. 4).

Figure 5:
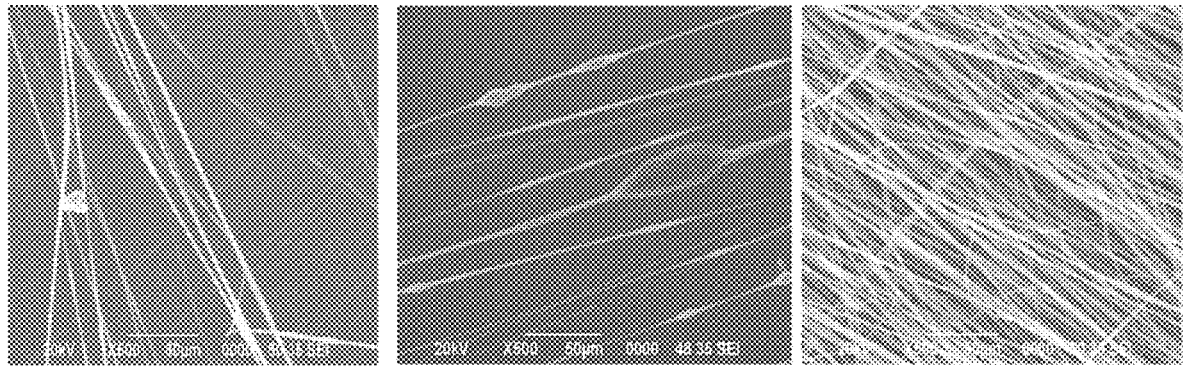
FIG. 5 includes SEM images that illustrate the impact of applied voltage on the PVDF fiber morphology (10 kV, 30 kV, 20 kV from left to right).
Figure 6:
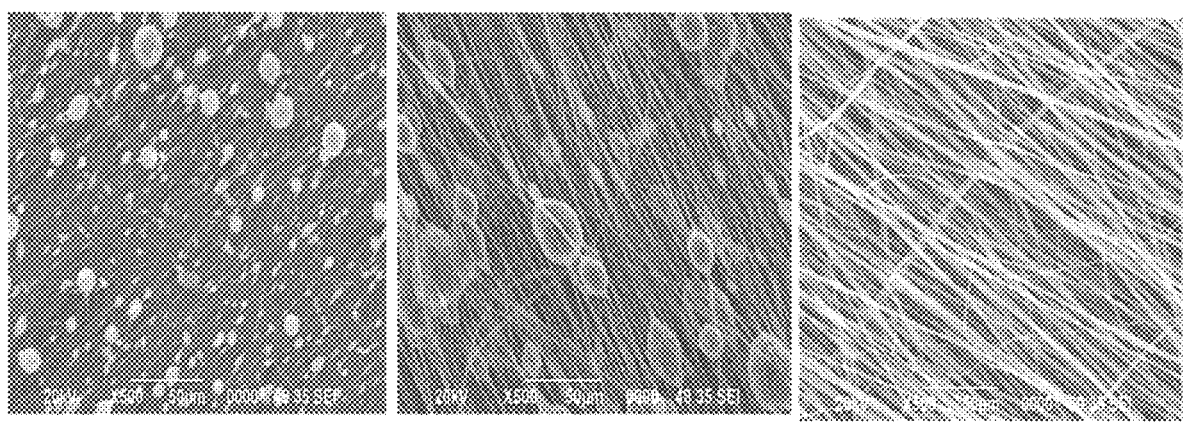
FIG. 6 includes SEM images that illustrate the impact of solvent concentration on the PVDF fiber morphology (100% DMF, DMF:Acetone (80:20), DMF:Acetone (60:40) from left to right).
Figure 7:
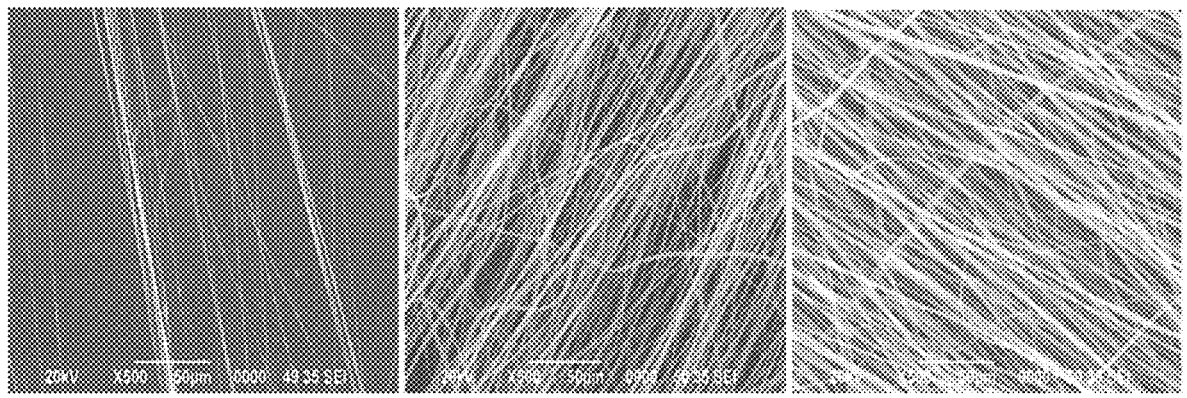
FIG. 7 includes SEM images that illustrate the impact of flow rate on the PVDF fiber morphology (0.005 ml/min, 0.1 ml/min, and 0.01 ml/min from left to right).
Figure 8:
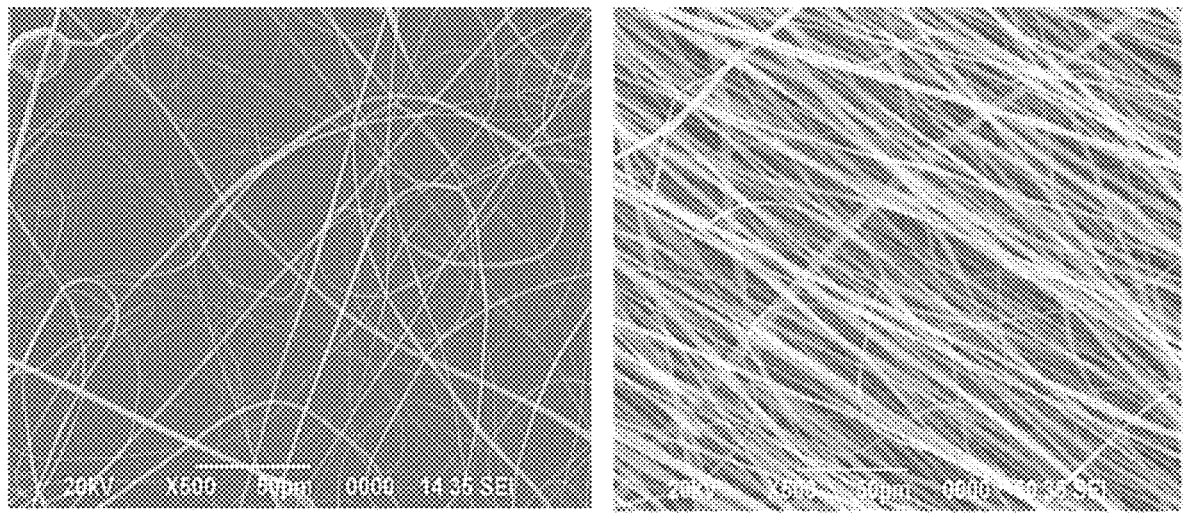
FIG. 8 includes SEM images that illustrate the impact of collector drum size on the PVDF fiber morphology (1 cm and 2.5 cm from left to right).

Applied voltage is another parameter that plays a significant role in the electrospinning of fibers. According to the results (FIG. 5), an increase of the applied voltage led to the increase in the number of drawn fibers only in a specific range (20 kV) as 10 kV was not strong enough to draw fibers. Higher voltage, such as 20 kV, helps to increase the density of the fibers. On the other hand, voltage higher than 20 kV, such as 30 kV, led to a decrease in the number of fibers since the fibers can get distracted from collecting around the collector. The distraction of fibers from the collector was due to the high potential difference of the positive electrode and not only the grounded collector but also the electrospinning chamber. It was observed that fibers stuck to the chambers as well as the collector. Therefore, lower voltages and also higher voltages may result in the low efficiency of the fiber production. FIG. 6 shows the influence of solvent constitution on fibers consistency. While DMF was used as the main solvent for PVDF, acetone can be used as the co-solvent. It was observed that an increase in the ratio of acetone to DMF reduces the defects such as beads and increases the consistency of the fibers. The flow rate of polymer solution could also have an impact on the density of the drawn fibers. As observed in FIG. 7, as the flow rate was increased from 0.005 ml/min to 0.1 ml/min, the density of the fabricated fibers increased significantly. Finally, the size of the drum used to draw the fibers is another important parameter that led to a considerable improvement in the alignment as well as the density of the fabricated fibers. FIG. 8 shows the changes affected in PVDF fiber morphology as the radius of the drum changed from 1 cm to 2.5 cm.

Figure 9:
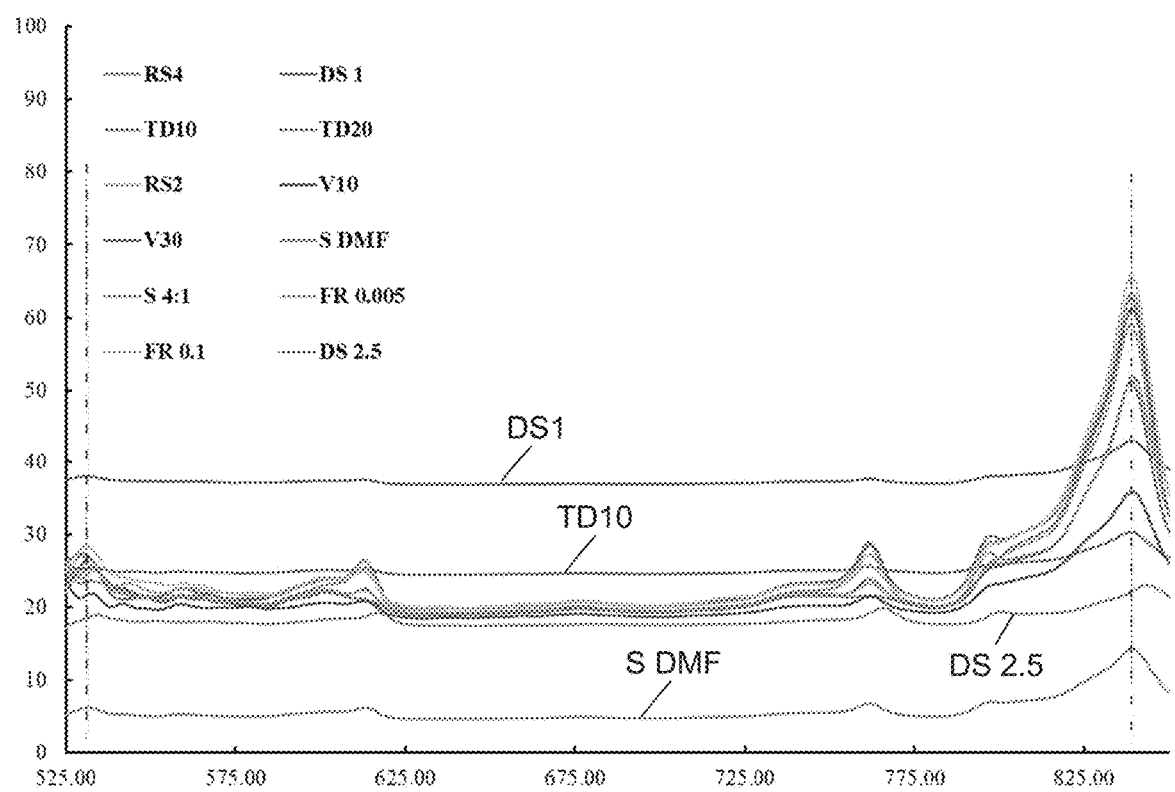
FIG. 9 is a graph that shows attenuated total reflectance-Fourier transform infrared spectroscopy (ATR-FTIR) results of PVDF fibers.
Figure 10:
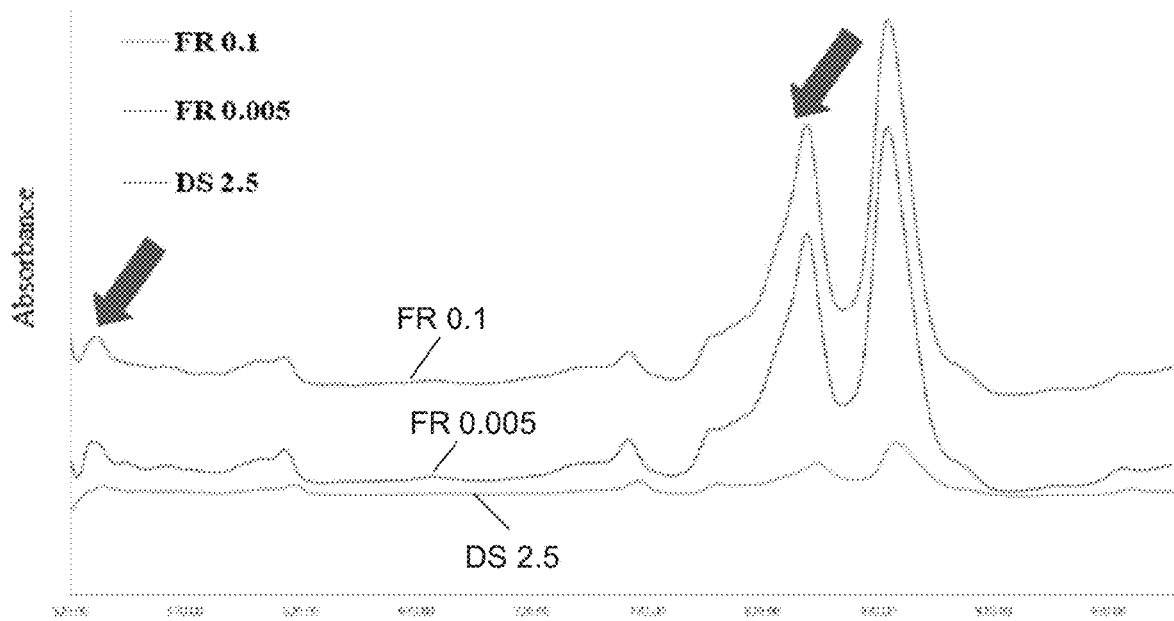
FIG. 10 is a graph that shows the impact of flow rate on polymorphism of PVDF fibers.
Figure 11:
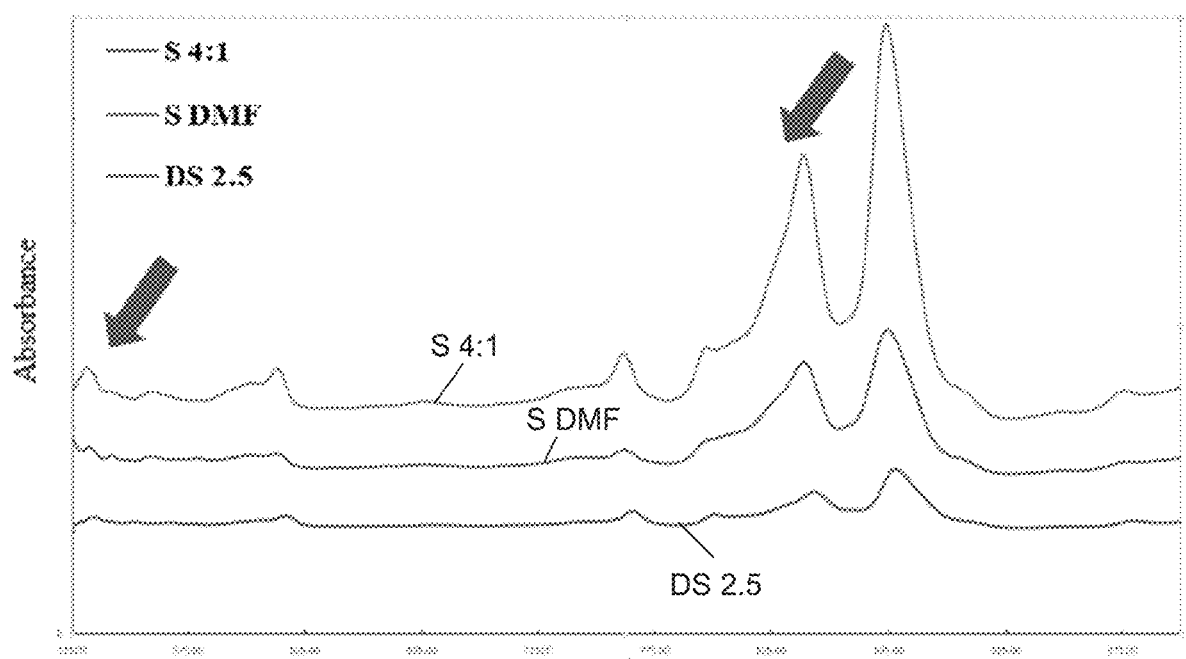
FIG. 11 is a graph that shows the impact of solvents on polymorphism of PVDF fibers.
Figure 12:
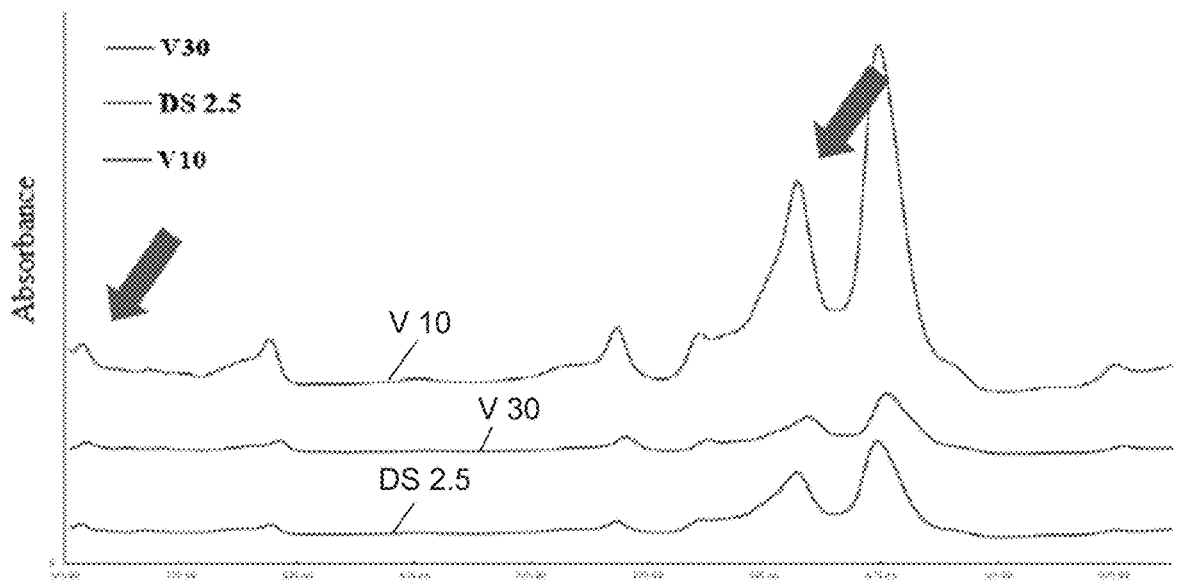
FIG. 12 is a graph that shows the impact of applied voltage on polymorphism of PVDF fibers.

In order to evaluate the polymorphism of PVDF, the β ratio was measured quantitatively. Infrared absorption bands at 530 and 840 nm (from ATR-FTIR results) were used as the characteristics of α and β phases, respectively. Infrared absorption at relative fraction of β phase can be calculated though Equation 1. FIG. 9 shows the ATR-FTIR results of the fibers. FIG. 10 shows the ATR-FTIR results of the samples with different flow rates. As can be observed in FIG. 11, the β ratio is as low as 6% in the samples prepared with flow rate 0.005 ml/min and it increased significantly to about 28% with the flow rate 0.01 ml/min. There was a decrease (28%) for the samples prepared with a flow rate 0.1 ml/min. FIG. 12 shows the impact of solvent ratio on the β phase. As a result of adding acetone to the PVDF solution, the β ratio increased gradually in the samples SDMF, S 1:40, and 40:60 from 13 to 89%.

Figure 13:
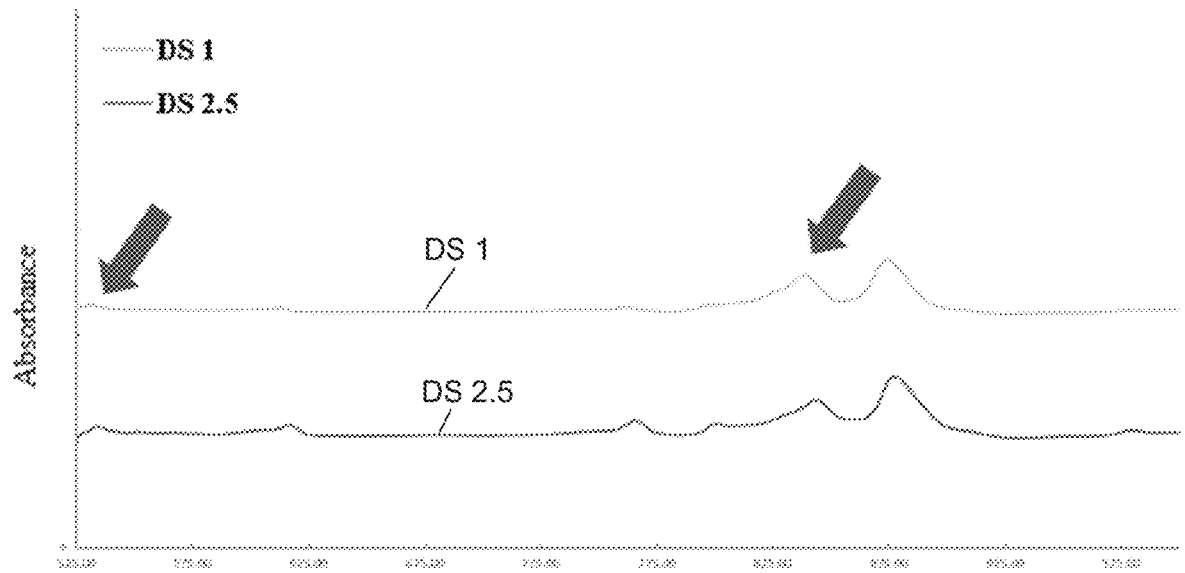
FIG. 13 is a graph that shows the impact of on drum size polymorphism of PVDF fibers.
Figure 14:
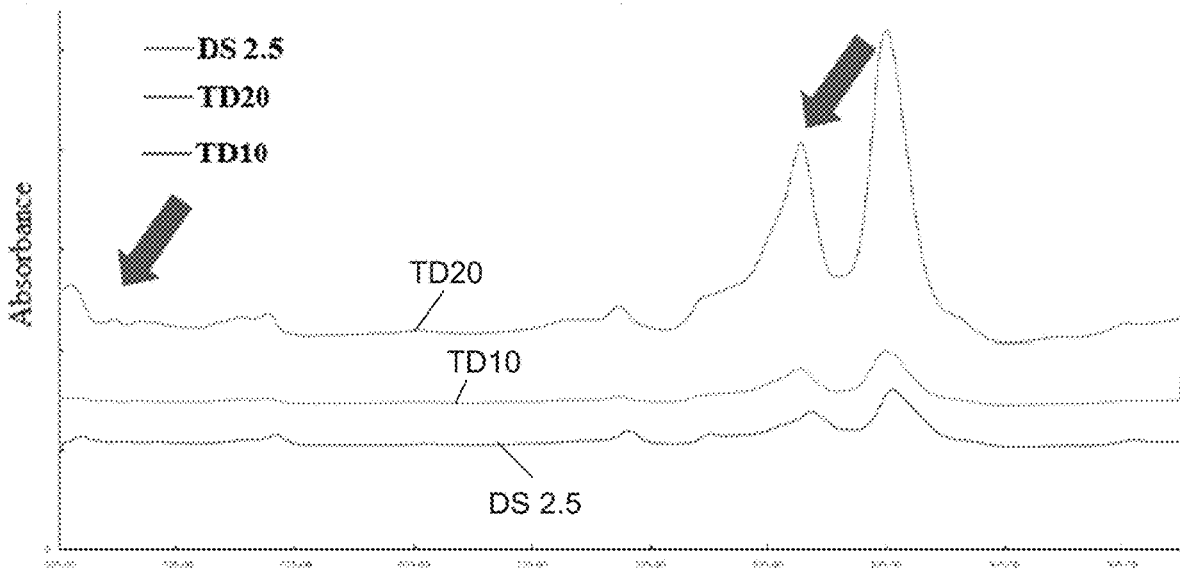
FIG. 14 is a graph that shows the impact of traveling distance on polymorphism of PVDF fibers.
Figure 15:
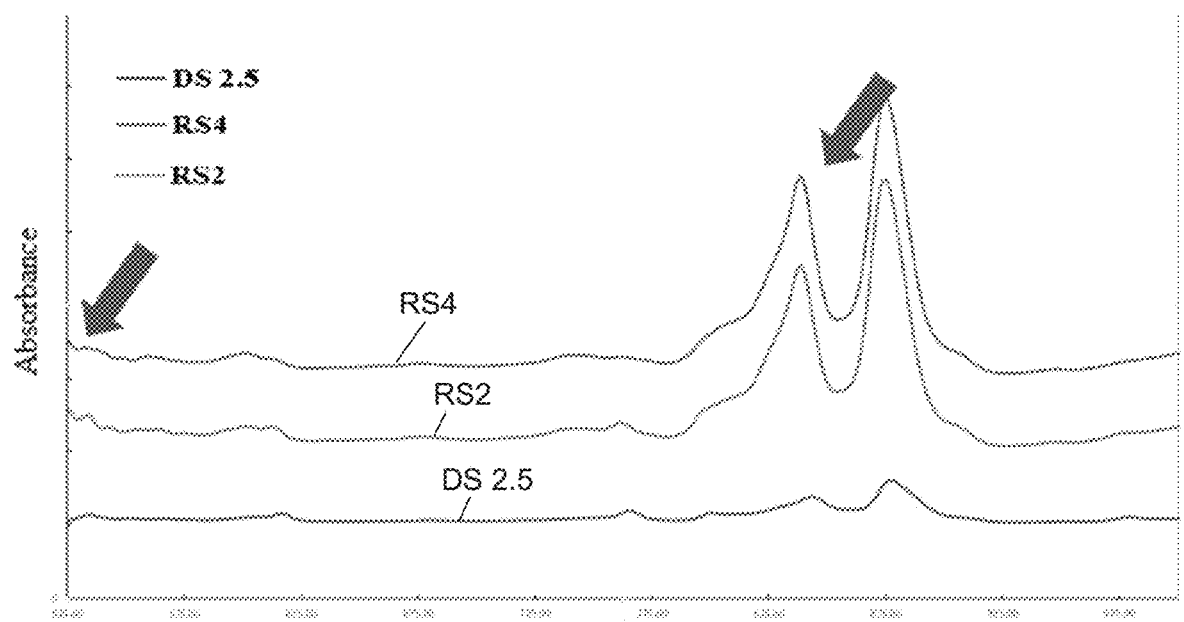
FIG. 15 is a graph that shows the impact of rotating speed on polymorphism of PVDF fibers.

In addition, applied voltage could lead to changes in β ratio. As seen in FIG. 13, the β ratio of the samples prepared at 10 KV and 20 kV was about 89%, while this ratio decreased to 13% when samples were prepared under 30 kV. It is assumed that this change in the V30 is due to the distraction of the fibers, resulting in the drum being unable to stretch the fibers which is a necessary aspect of β phase formation. It was also observed that the traveling distance between the collector and the syringe plays a prominent role in β phase configuration. FIG. 14 shows that the β ratio could increase as the traveling distance increases with the samples TD10, TD20, and TD30 having β ratios of 54, 64, and 89%, respectively. Drum size is another parameter which led to a significant change from 48 to 89%. As shown in FIG. 15, it is suggested that the reason for this increase was due to the impact of the size of the drum in collecting the aligned fibers. Hence, fibers were stretched appropriately such that it caused an increase in the β ratio in DS2.5 in comparison to DS1. It was observed that the speed of collector rotation exerted an influence on β ratio as well. The β ratio increased from 22% in the sample RS2 to 35% in RS4 and finally it reached to 89% in the sample with rotating speed 6.

Figure 16:
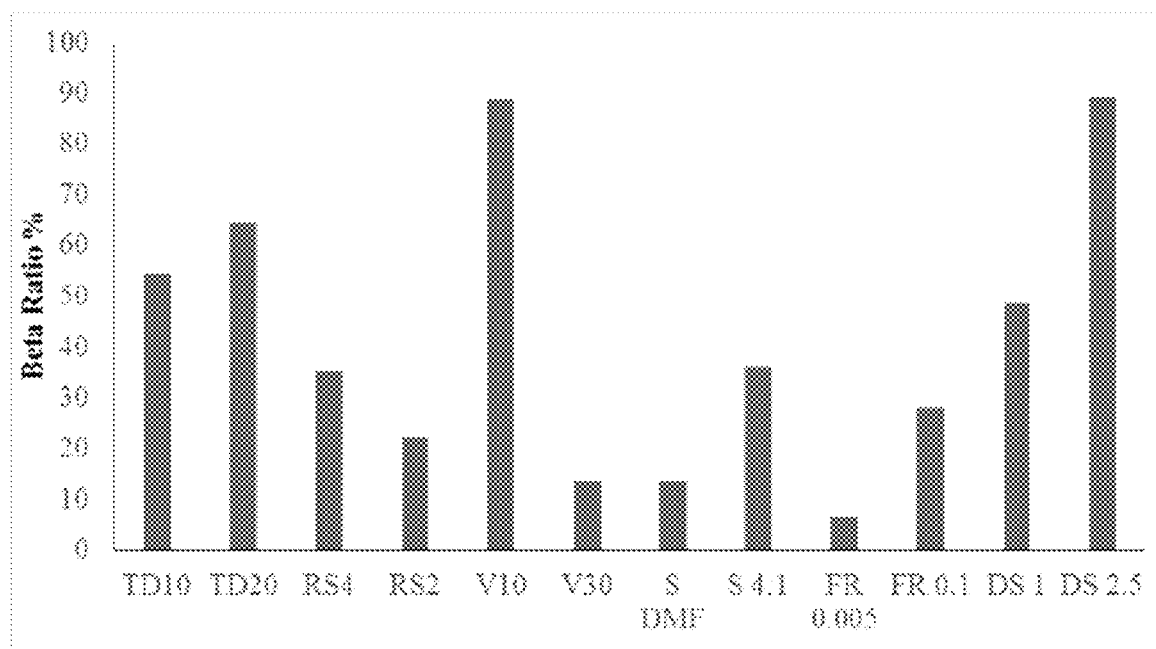
FIG. 16 is a graph that provides a summary of beta ratio the groups detailed in Table 1.

FIG. 16 shows the calculated β ratio for each sample identified above. According to the ATR-FTIR results, there are some samples with the highest β ratio in comparison to the others. Specifically, the increase in rotator speed from 470 to 1410 rpm led to an increase in the β ratio from 22 to 89%. Also, adding acetone to the PVDF solution increased the β ratio from 13 to 89. In addition, the size of drum affects the β ratio such that the increase drum radius can turn β ratio from 50 to 89%. Finally, the flow rate plays an important role in the β crystal formation as the β ratio increase from 6.5 to 89.

From the results of the morphology and polymorphism of the PVDF fibers, the most optimized sample (DS2.5) with 89% β ratio was chosen for further studies and coating with PPy.

Figure 17:
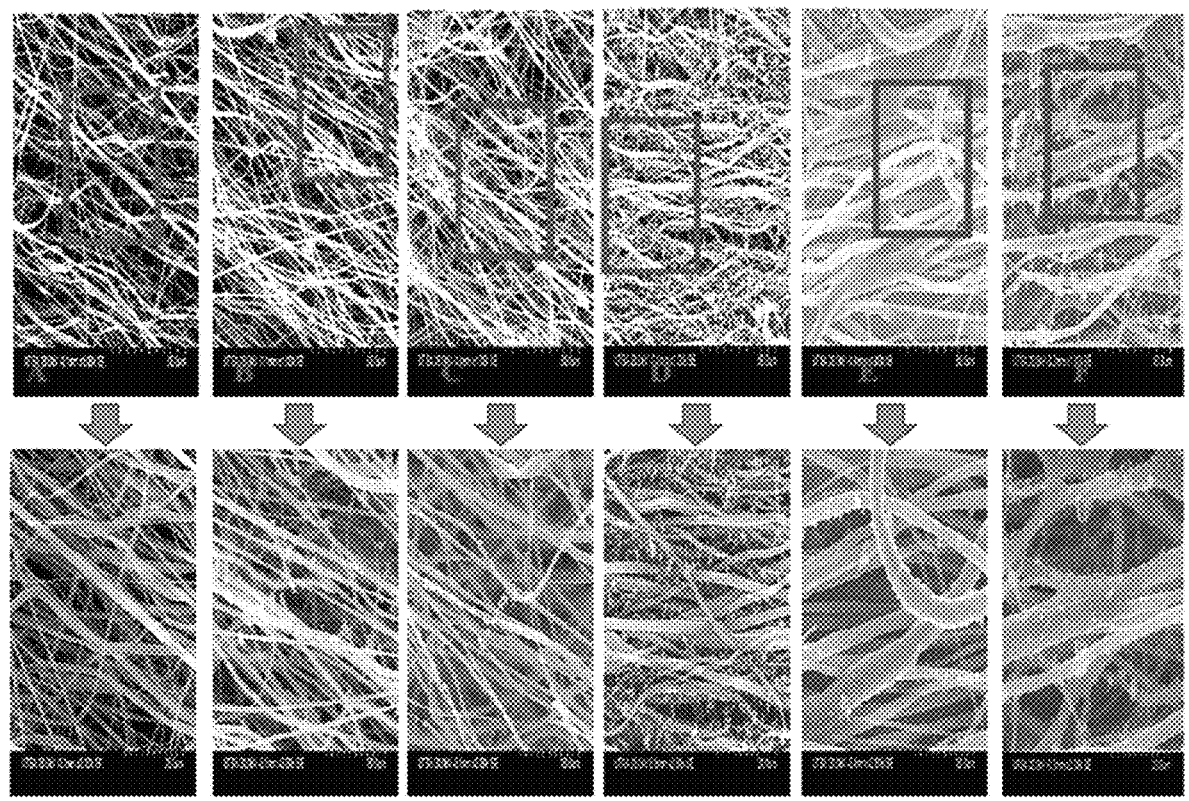
FIG. 17 includes SEM images of PVDF fibers and PPy-coated PVDF fibers with two magnifications (1K and 2K). A) uncoated PVDF fiber B) PPy coated PVDF fibers after 1 hour B) 2 hours C) 6 hours D) 12 hours E) 18 hours F) 24 hours.
Figure 18:
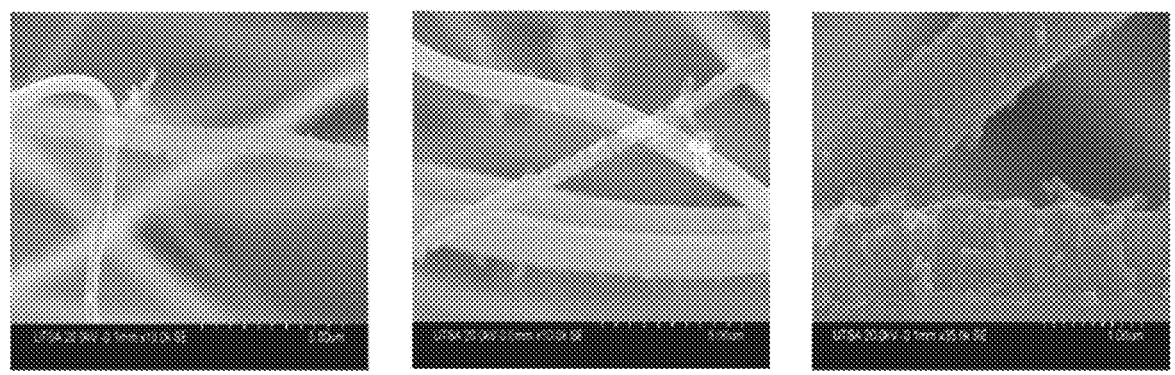
FIG. 18 includes SEM images of PPy-coated PVDF fibers in higher magnifications.

After coating the PVDF fibers with PPy containing biotin, SEM images were taken with higher magnification in order to prove the PPy coating layer on PVDF fibers. According to FIG. 17, after one hour of polymerization, PPy debris was present while no significant coating was observed. The amount of PPy debris increased after 6 hours and also partial coating was observed. After 12 hours of polymerization, the amount of free debris was higher than previous fibers while the thickness of the fibers increased. Eighteen hours of polymerization provided a consistent coating with lower unattached PPy debris. The samples after 24 hours of polymerization were coated while the debris was more present in comparison to the samples with 18 hours of polymerization. Moreover, FIG. 18 represents the quality of coating in higher resolutions and exhibits how the PPy has coated the PVDR fibers.

Figure 19:
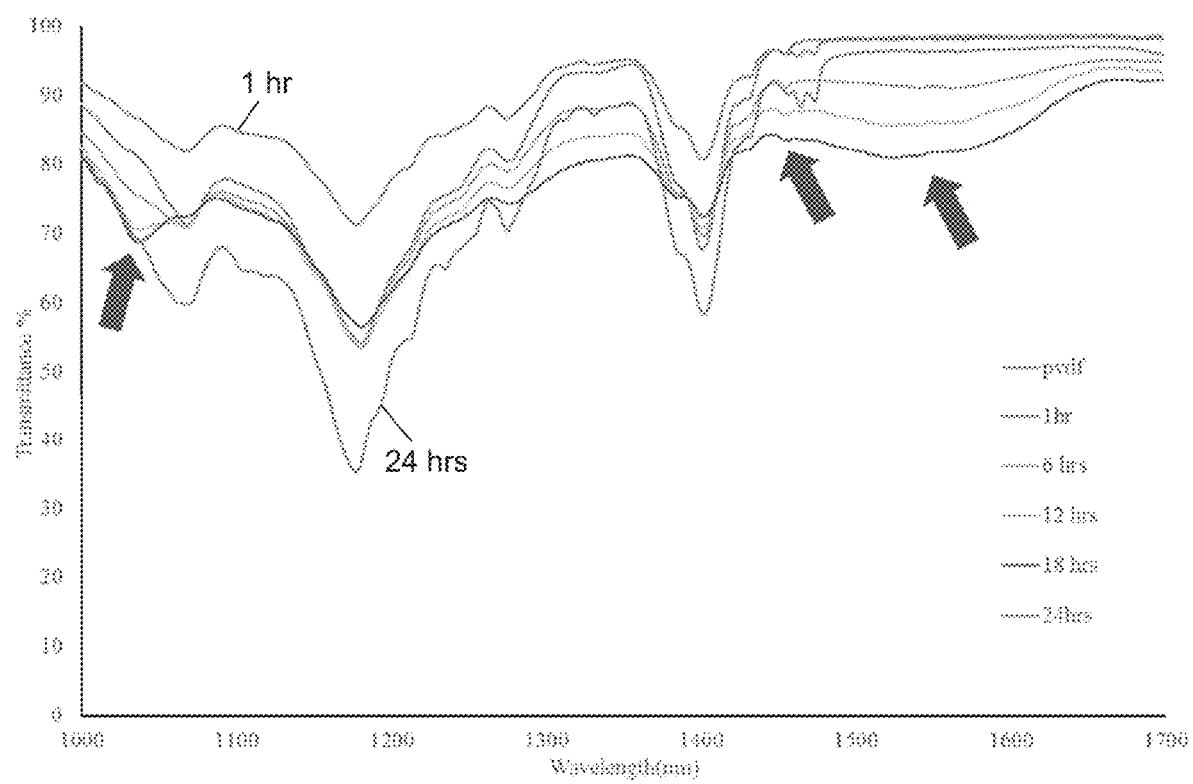
FIG. 19 is a graph that shows ATR-FTIR results of PPy-coated PVDF fibers.
Figure 21:
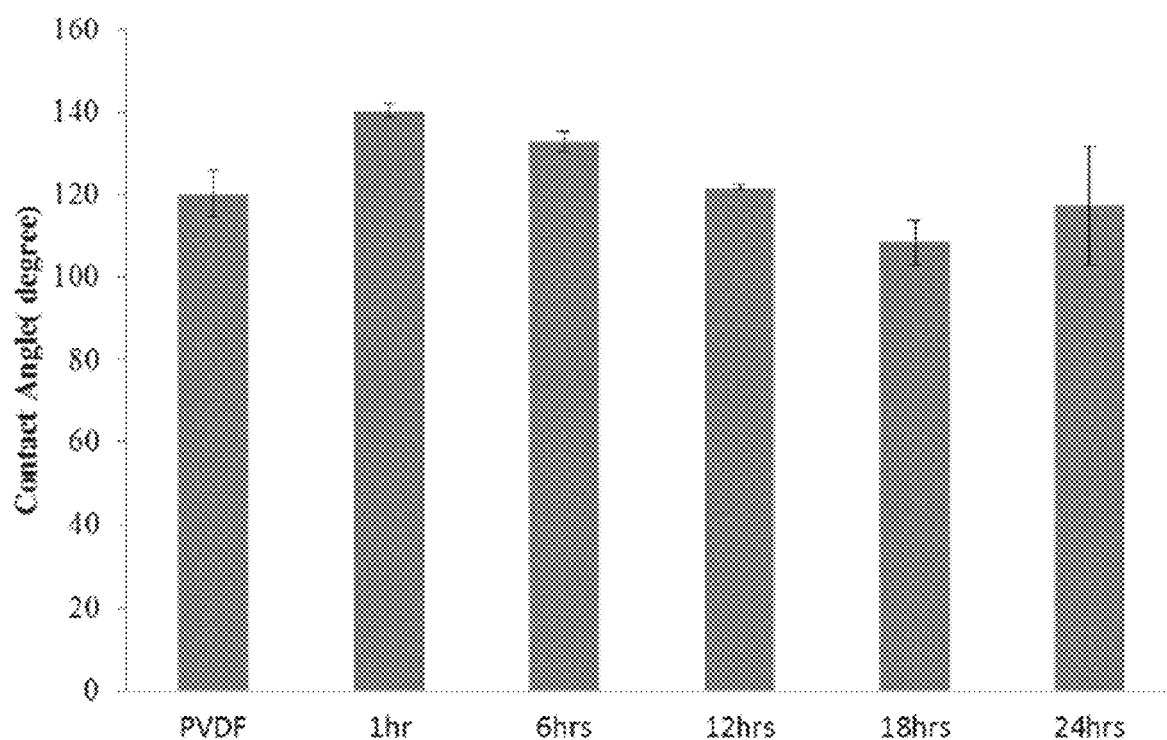
FIG. 21 is a graph that provides contact angle results of PVDF fibers and PPy coated PVDF fibers after 1, 6, 12, 18, 24 hours of polymerization.

Characteristic PPy bands are shown in FIG. 21. The ATR-FTIR results of coated samples after 1, 6, 12, 18, and 24 hours of polymerization proved the impact of coating on different bands. In general, biotin shows asymmetric and symmetric carboxylate stretching absorptions at 1674, 1546, and 1407 $cm^{-1}$, respectively. In addition, pure PPy shows absorption at 1040 $cm^{-1}$ and 1540 $cm^{-1}$ in plane C-H, 1459 cm corresponds to the C-N stretching in the pyrrole ring, and 1165 represents the C-N stretching vibrations. As specified by FIG. 19, the absorption at 1546 $cm^{-1}$ increased as the time of polymerization increased. Also, minor changes could be observed at 1459 $cm^{-1}$ and higher absorbance for the samples after 24 hrs polymerization at 1040 $cm^{-1}$.

Figure 20:
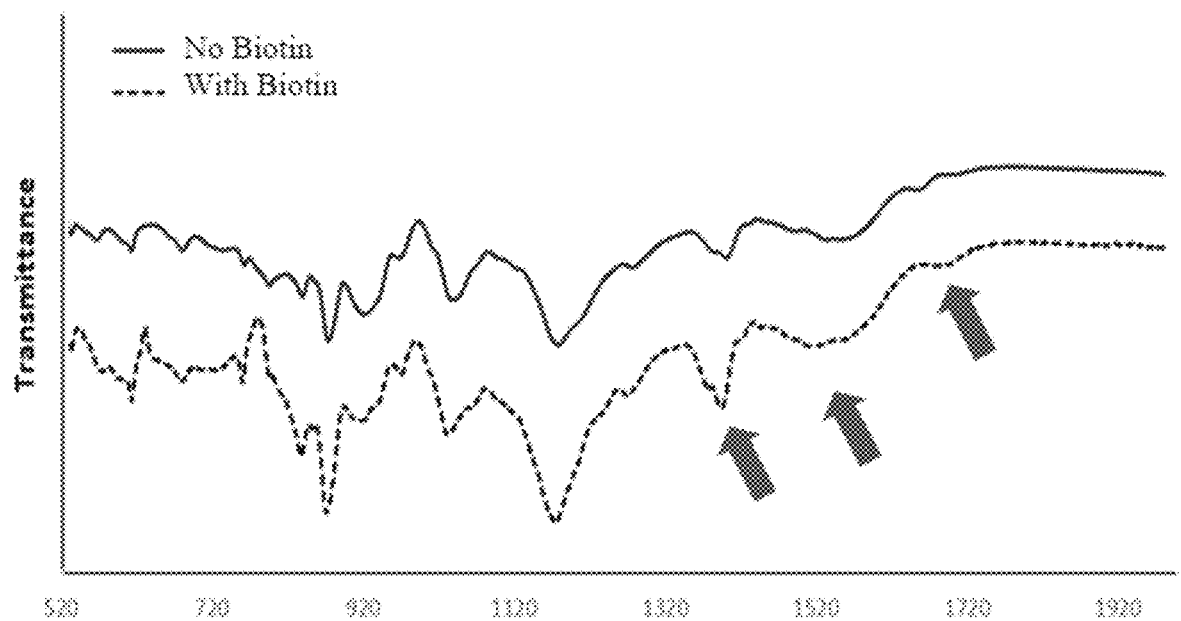
FIG. 20 is a graph that shows ATR-FTIR results of coated samples with and without biotin.

ATR-FTIR results of the samples with and without biotin as the co-dopant indicated the contribution of biotin in the polymerization of PPy (FIG. 20). The peaks at 1674, 1546, and 1407 $cm^{-1}$, which are responsible for the asymmetric and symmetric carboxylate stretching absorptions, showed higher transmittance intensity in the sample without biotin in comparison to the regular sample with biotin.

Hydrophlicity of PVDF fibers and PPy coated PVDF fibers for 1, 6, 12, 18, 24 hours of polymerization was characterized via the sessile drop technique. According to the results (FIG. 20), the contact angle increased in the fibers polymerized for one hour and it decreased as the polymerization time increased. Finally, the contact angle increased again after 24 hours of polymerization. This might be the result of free debris, which affects the morphology of the surface and it is not smooth. Hence, the contact angle increases consequently. According to the SEM images, the debris was decreased in samples 6, 12, and 18 hours and once could observe the increase of the debris decrease but due to the increase of the debris again in sample 24 hrs.

In order to evaluate the impact of PPy debris, the debris was removed from the surface for the sample with the highest contact angle, which is one hour of polymerization. FIG. 21 shows that debris removal could decrease the contact angle from 141° to 82°, which is due to the smoother surfaces.

In order to evaluate the amount of available streptavidin in each sample, the aliquot containing remained streptavidin was kept and the absorbance of unconjugated streptavidin was evaluated. According to the loading efficiency results, 88±1% of the streptavidin was conjugated and the release study is based on the total amount of streptavidin used initially.

Figure 22:
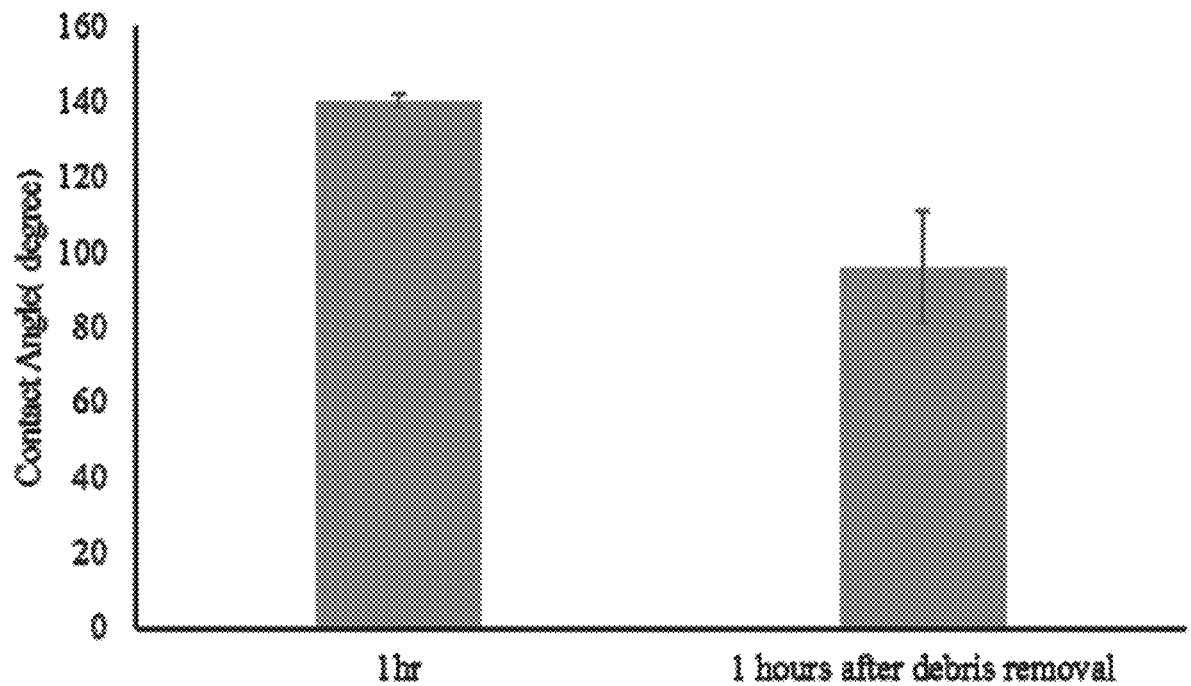
FIG. 22 is a graph that provides contact angle of PPy coated PVDF fibers before and after debris removal.

The triggered release of capabilities of the PPy coated PVDF fibers were characterized first only based on biotin-streptavidin HRP conjugations and the impact of the voltage on the release. FIG. 22 exhibits the release of biotin-streptavidin HRP relies on the amount of electrical stimulation applied to the system, although the prescribed voltage is 5 V/cm for muscle regeneration purposes.

According to the FIG. 22, higher voltages caused higher release of the growth factor complex. This proves an electro-responsive release of the growth factor complex. Low voltages, such as 3.5 V, led to the low growth factor release during the first 5 minutes and the release increased when 5 V applied to the samples. In addition, higher voltages led to the higher release similar to the burst release. It was concluded that low voltages may work as a suitable method to have a constant release without any burst release while higher voltages may cause the burst release and also hydrolysis. Therefore, the rest of the drug release studies were conducted based on 5 V/cm, which would be beneficial for the muscle regeneration as well.

Figure 23:
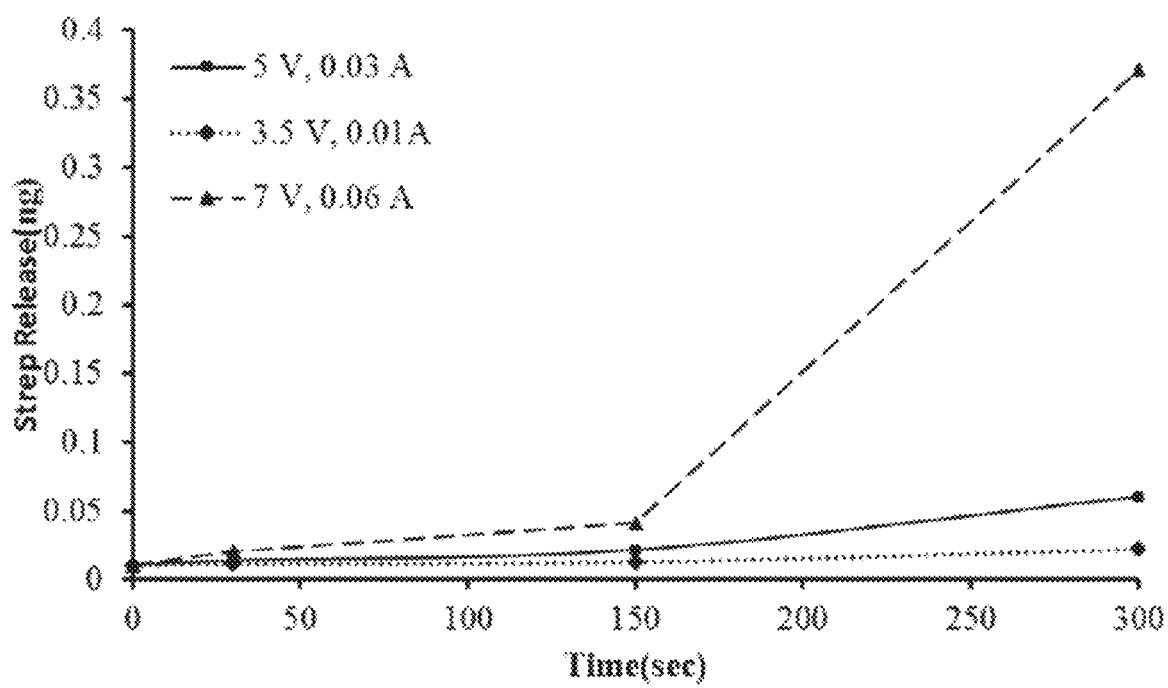
FIG. 23 is a graph that shows streptavidin release based on different electrical stimulations.

FIG. 23 shows the results of biotinylated bFGF release in the first hour of stimulation. The release of bFGF increased gradually in two phases (P<0.001). For the first 24 minutes, the release of the growth factor complex was higher than the rest of the experiment.

Figure 24:
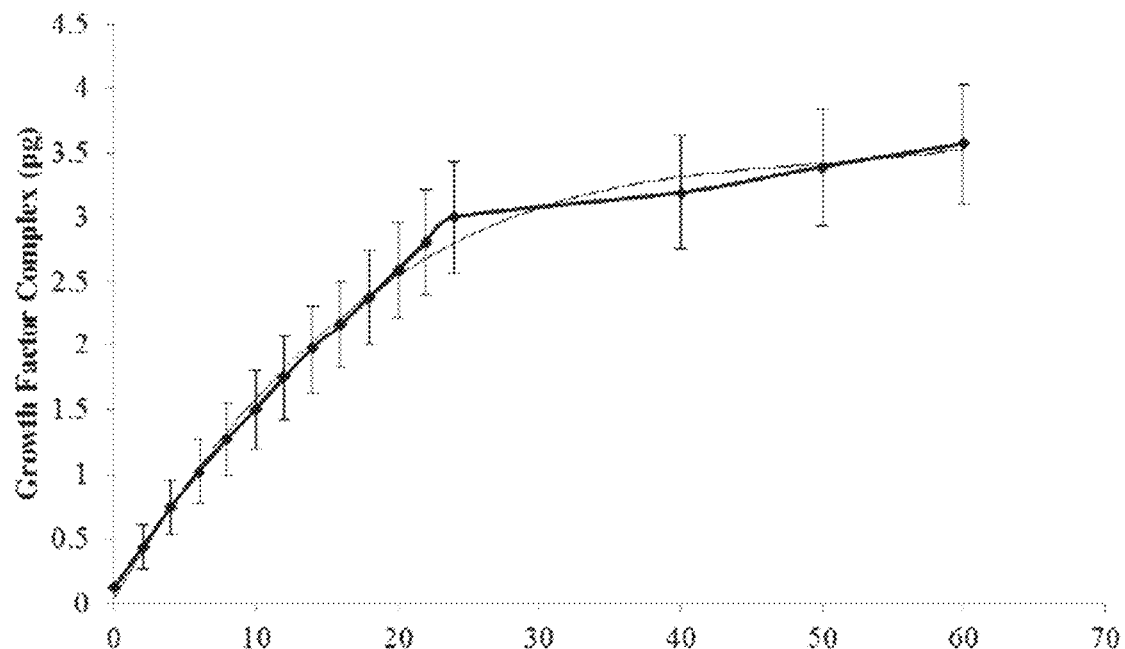
FIG. 24 is a graph that shows basic fibroblast growth factor (bFGF) release in the first hour of stimulation.

FIG. 24 exhibits the impact of bFGF, biotinylated bFGF, the released growth factor complex, and also the delivery complex without bFGF. According to the results, non-conjugated growth factor and biotinylated growth factor are biologically active and are caused to the higher cell proliferation in comparison to the negative control sample which is the cell suspension without any additives. The results of the growth factor complex without conjugated bFGF indicate that the complex without the growth factor has no impact on cell growth while conjugated growth factor to the complex led to the cell death.

Discussion

Reconstruction of functional musculoskeletal tissues is a critical need, however, conventional methods have not been successful in many cases. The availability of novel, active stimulatory biomaterials for tissue engineering will open a new pathway for the controlled regeneration of functional musculoskeletal tissues. The approach described above revolved around developing a novel scaffold design that provides smart drug release by leveraging the unique properties of piezoelectric and conducting polymers for translational applications in regenerative medicine. The polymerization method presented in the studies is also uniquely suited for the loading of growth factors into a local depot for smart growth factor release during tissue regeneration.

In the studies, the design was based specifically on PVDF, a biocompatible polymer with very high piezoelectricity and PPy, a biocompatible conducting polymer used widely in neural tissue regeneration and for applications in biosensors. Taking biomimetic cues from the extracellular matrix architectural organization, it was intended to design the substratum during fabrication as a dense sheet of preferably aligned fibers. One of the fabrication techniques available to prepare polymer micro-fibrous architectures with tunable morphology is the technique of electro-spinning. Given the advantages of electro-spinning as a manufacturing technique to enhance the piezoelectric properties of PVDF using the strong electric field during fabrication, the optimization of various processing parameters was essential to ensuring the maximum transformative efficiency of the substrate between mechanical strains and external electrical fields. Travelling distance, collector drum size and rotating speed, source voltage, co-solvent ratio, and polymer blend flow rate were all varied in turn to optimize the fibers obtained, such that they had a smooth, aligned morphology as qualitatively observed under SEM observation and simultaneously demonstrated elevated piezoelectric properties, as quantitatively demonstrated by an increased β ratio. This was demonstrated for a collector drum size of 2.5 cm, rotating at 1410 rpm, 30 cm away from polymerization blend dissolved in a 3:2 w:w ratio of acetone to DMF being extruded at a rate of 0.01 ml/min with a 20 kV potential difference applied between syringe tip and collector.

While PVDF is a polymer with strong piezoelectric properties, a lack of direct drug loading capacity and hydrophobicity of this polymer are the main limitations preventing its use in the body for regenerative medicine or as a stimulatory testing platform for in vitro studies. In order to take advantage of PVDF's potential, it was proposed to utilize a secondary biocompatible conducting polymer as a coating.

PPy was chosen for the coating of the aligned PVDF fibers to generate a platform for an electroactive polymeric composite of a piezoelectric polymer with a conducting polymer. The novelty lies in the in situ polymerization of the PPy on the surface of the PVDF, which allows for later growth factor loading within the PPy coating. Generally, there are some limitations with the use of PPy, such as limited polymerization methods and poor drug loading capacity. The primary limitations of the current polymerization methods is that they mostly employ electrochemical deposition techniques, which is limited by ability to only coat conductive materials which can form electrodes in the galvanic cell. By using the in situ polymerization method, and modifying it for effective growth factor release, one is able to circumvent the most common limitations of both the individual polymers for biomedical applications while harnessing the biochemical and biophysical stimulatory properties of the composite system for potential tissue engineering applications.

As previously mentioned, the hydrophilicity or lack thereof of PVDF fibers and PPy-coated PVDF fibers is of great interest for biomedical applications since the attachment of proteins/peptides on the material substrates, and the subsequent attachment and migration of cells, is significantly inhibited on hydrophobic substrates. This was one of the reasons for preferring a PPy coating, anticipated to be hydrophobic on the fairly hydrophobic PVDF surface. Experimental characterization using the sessile drop technique demonstrated that the contact angle initially increased for 1-hour polymerization duration and then decreased with an increase in polymerization time as anticipated until 18 hours of polymerization. Non-intuitively, the contact angle increased again beyond 18 hours of polymerization. It is hypothesized that after a uniform coating thickness and consistency of PPy is achieved on the substrate, changes in surface coating morphology as a result of free debris entangled with the coating might increase surface roughness. This rougher surface is much more like the non-uniform 1-hour polymerization time and would explain the contact angle increase. This hypothesis was also supported by the SEM evaluation, which indicated visible decrease in debris at polymerization times of 6, 12, and 18 hours with an increase in the surface debris with 24 hrs of PPy polymerization. This design made this method ideal for polymerization involving temperature sensitive chemicals such as biological agents, which might be denatured at elevated temperatures.

It is hypothesized that in situ polymerization provides a system able to uptake the growth factor after the polymerization through the contribution of biotin as the doping agent without the burst release or growth factor leakage.

This method might be the result of free debris which affects the morphology of the surface and it is not smooth; hence, the contact angle increases consequently. Therefore, 1 hour of sonicated washing removed the debris and reduced the contact angle (resulting in the only test group with a contact angle <90°), which further supports the free polymer chain induced hydrophobicity and the need for extensive cleaning of the materials prior to applications being a necessary step.

The regeneration of tissues in the human body is a complex biochemical interplay between cellular and molecular signaling closely regulating the regenerative micro-environment. Growth factor-based stimulation of locally responsive cells has been an invaluable tool in the regenerative medicine arsenal. In order to provide a one-step solution for musculoskeletal regenerative materials, one central objective is to load a growth factor payload onto novel biomaterial substrates developed, with best-case scenario of the growth factors being released from the depot on active demand during the tissue regeneration process.

One of the primary proof-of-principle findings from this research was the ability to release streptavidin-tethered growth factors, bFGF in this study, from a PPy-coated PVDF substrate upon the application of electrical stimulation. This exercise involves the demonstration of multiple milestones, including the ability to large a high payload or a depot for the drugs to be delivered, the efficiency and reproducibility of the release, minimal unintended release without active stimulation, and, finally, the retention of biological activity of the delivered growth factor at the biological target.

Muscle cells exhibit enhanced formation of striations and contractile protein expression under electric field above 5 V/cm. Hence, the drug release experiment will be specifically conducted electrical stimuli based on the mentioned electric field.

The application of different levels of electrical voltage for different durations was used to demonstrate the functionality and active control of drug delivery from the PPy coating. The growth factor in the case of this model is released not as a free protein but as 3 proteins tethered to a streptavidin core. The reason for this is the mechanism of release: the avidin-biotin linkage is very stable and forms a stable biotinylated protein-streptavidin complex. Upon application of an electrical stimulus, it is hypothesized that the biotin used as a co-dopant in the polymerization of the PPy is freed from the polymer matrix, releasing the tethered drug-streptavidin complex. It was observed that increasing the applied voltage caused higher release of the growth factor complex. This proves the electro-responsive release of the growth factor complex. Low voltages (e.g., 3.5 V) led to low growth factor release during the first 5 minutes and the released dose could be increased when a higher voltage (e.g., 5 V) was applied to the samples. At even higher voltages (e.g., 7 V) an even greater release was observed, which was similar to the burst release observed in physical adsorption based delivery of growth factors. These observations enable one to posit that low voltages can potentially be used as a suitable method to have a constant release without the early burst release that has been shown to be deleterious with degradation or diffusion based release systems, while higher voltages may cause the burst release as well as potentially hydrolysis. This may have a specific benefit in the case of skeletal muscle regeneration for example, where 5 V is the typical electrical stimulation regimen used to stimulate the contraction of muscle to act as a motor neuron impulse surrogate after injury and during tissue engineering.

From the loading efficiency evaluation in the studies, it was found that 88±1% of the streptavidin was conjugated to the biotin used as the co-dopant for the polymerization of the PPy. This leads one to hypothesize that the control of the quantity of the biotin in the PPy coating and the total thickness of the PPy coating can both be used as a means of modifying the total capacity of drug that can be loaded onto the material in a quantifiable manner.

The extended release of the bFGF was quantified for a total 1 hour of continuous stimulation. The primary purpose of this experiment was to evaluate material fatigue, responsiveness for prolonged delivery, and to understand the changes in release kinetics as the reservoir volume of the drug loaded gets depleted. The release of bFGF was observed over the entire hour of stimulation, which was promising, but occurred in two distinct phases. For the first 24 minutes, the release of the growth factor complex was higher and seemed to be a linear cumulative release rate in response to duration of stimulation, while for the next 36 minutes the cumulative release rate was significantly lower. Over the full hour, 3.57 pg, which is 10.9% of the total drug loaded, was released.

One of the potential applications of this platform technology is in the form of an implanted drug-depot which would then be stimulated to release the growth factor payload upon external/internal stimulation when desired/programmed. To perform in that manner, it is required that the drug depot be stable and survive with a majority if not all of the tethered payload intact until stimulated. If there was potentially a leakage current of unstimulated release or there was significant substrate degradation based loss of either the loaded drug or the release system, then the application as an implantable reservoir would not work without additional protection for the carrier. The stability of growth factor loading samples was examined after keeping the samples in PBS for two months. Finally, a growth factor release study was conducted on samples and after one hour 0.024 pg of the streptavidin was released, which is 8±0.4% of the total release from the fresh samples over the same time. This indicates that without additional modification, the drug loaded PVDF:PPy carrier is not feasible as a long-term release system for active delivery.

Basic fibroblast growth factor (bFGF) was used as a model drug to evaluate the capability of the PVDF-PPy system to deliver a growth factor upon electrical stimulation while maintaining the bio-activity of the delivered growth factor. Bioactivity of the eluent was evaluated using BALB 3t3 cells, an embryonic mouse cell line which have been previously used for the standardization of bFGF dose response based proliferative activity. Similar results were observed, with free bFGF and biotinylated bFGF demonstrating an increased proliferation of the cells compared to the blank controls of media alone and biotin-streptavidin complex alone with no conjugated growth factors. The counter-intuitive results were observed for the released growth factor complex, which is streptavidin conjugated to 3 biotinylated bFGF molecules and one biotin. The eluent from the release study of this group had a surprisingly negative result on the BLAB 3t3 cells, showing almost no cell viability after exposure. Since it was demonstrated using the non-bFGF conjugated release that the electrical stimulation is not causing any material based elution products which are cytotoxic, it is reasonable to hypothesize that the bFGF conjugated payload is indeed being delivered, but is acting in a manner that is cytotoxic.

It is hypothesized that it is the nature of the complex to which the bFGF is tethered, which plays a role in causing cell death. Denatured growth factor or delivery complex without bFGF may have no effect on the cells but as soon as a bioactive growth factor binds to the delivery complex, it binds to the fibroblast growth factor receptors, indicating that the protein itself and its functional site are not significantly affected by the release, and potentially initiates unintended further interactions.

Figure 25:
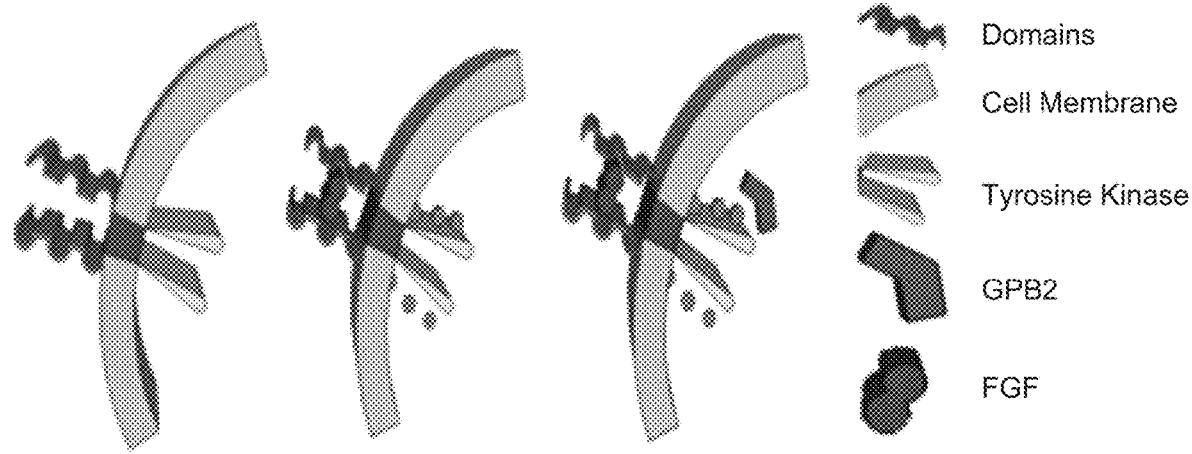
FIG. 25 is a schematic diagram of fibroblast growth factor (FGF) receptors and the procedure of FGF conjugation.

There are two FGF receptors available in cell membranes: high- and low-affinity FGF receptors. Low-affinity FGF receptors require heparan sulfate proteoglycans to be activated and it is assumed that their responsibility is to transfer the bFGF to high-affinity receptors. It has been reported that low-affinity receptors cannot internalize toxins but high-affinity receptors can. Also, low-affinity receptors can be transferred into the high-affinity receptors. High-affinity receptors are present during embryonic development such as BALB 3t3. Also, it is possible for the low-affinity receptors to be transformed to high-affinity receptors under various conditions, such as injury conditions, higher concentration of receptors by mass action, and in vitro conditions by chemical treatment. Moreover, both receptors can internalize the bFGF (FIG. 25), but when the FGF is conjugated to components that are toxic to the cells (e.g. saporin), the low-affinity receptors cannot internalize it and it could potentially have a deleterious effect on cell fate. This leads one to hypothesize that the multiple bFGF moieties bound to the streptavidin could potentially be blocking intracellular signaling and internalization of the complex by trafficking across the cell membrane leading effectively to cell toxicity.

Table 2 shows the size of FGFRs responsible for bFGF internalization. FGFs have considerable size heterogeneity. Natural FGF-2 usually has an 18 kDa mass, but larger forms also occur physiologically. The larger forms are localized in the cell nucleus rather than the cytoplasm. The mitogenic effect of FGF-2 has been linked to internalization to the nucleus, which leads to activation of nucleolar protein kinases and thus regulate ribosomal gene transcription. This has also been demonstrated specifically in the case of exogenously delivered FGF-2, which is internalized and translocate to the nucleus. There might be multiple issues with the size-dependent translocation and trafficking of bFGF and the resultant activation of proliferation. It is possible that the streptavidin bound bFGF complex is too large to be localized to the nucleus. Further evaluation of whether streptavidin conjugated with less than 3 biotinylated bFGFs also causes the same biological effects would need to be performed to test the proposed mechanistic hypothesis. A relative listing of the molecular weights of biotin, streptavidin and bFGF molecules is provided in Table 3.

TABLE 2

Fibroblast growth factor receptors specified for bFGF

| Name | Mass (KDa) | Variant | Specificity |
|---|---|---|---|
| FGF-R2 | 135 | IIIb and IIIc | FGF-1, 2, 7 and FGF-1, 2, 4 |
| FGF-R3 | 135 | IIIb | FGF-1, 2 |
| FGF-R4 | 110 | — | FGF-1, 2, 6 |

TABLE 3

Molecular weight of different components of growth factor complex

| Component | Molecular Weight(KDa) |
|---|---|
| Streptavidin | 53 |
| Biotinylated bFGF | 16.5 |
| Biotin | 244 |

Hence, the growth factor complex delivers the growth factor which remains biologically active but due to the size of the growth factor complex, it blocks further signaling and may result in unsuccessful internalization, and hence unsuccessful cell viability outcomes.

Therefore, one can conclude that the delivery complex released from the PPy-coated PVDF fibers has no negative effect on cell growth and proliferation. Moreover, the bFGF bound to the delivery complex remains active during the release as it demonstrably interacts with the FGF receptors on the cells. However, for regenerative medicine applications, a growth factor that is not internalized for functional bioactivity is probably a more advisable payload to be delivered from this system. In terms of potential biomedical applications though, in the cases when receptor targeted cell death is the desired outcome, such as in the case of cancers, it is possible that this system can be used for targeted delivery of streptavidin-conjugated complexes. A similar study has demonstrated the use of FGF conjugated with streptavidin and other functional proteins to traffic drugs across the blood-brain barrier and impact nerve cells by receptor binding.

CONCLUSIONS

The primary objectives of the research described herein were to develop a synthetic polymer composite which leveraged the synergy between piezoelectric polymers and conducting polymers to function as a stimulus response drug delivery platform. This work demonstrated the optimization of electro-spinning process parameters to produce PVDF fibers with an aligned morphology and maximized piezoelectricity. Furthermore, a novel in situ polymerization technique was developed to generate a uniform coating of PPy on the PVDF substrate obviating the need for conducting substrates and enabling multiple biomedical applications. The use of biotin as a co-dopant was leveraged to then load streptavidin-conjugated growth factors which could be released on electrical stimulation in a controlled manner and maintained activity upon delivery. Thus, the PVDF-PPy composite developed in this project is suitable as a platform technology for a variety of drug delivery applications in regenerative medicine and other areas of bio-medicine.

While the above disclosure has focused on biomedical applications, it is reiterated that the disclosed electroactive materials can be used in other applications. For example, an electroactive material of the type disclosed herein can be used in industrial applications, such as energy harvesting. One specific example of this is applications in which the electroactive material is integrated into a road surface. In such a case, compression from passing automobiles can be converted by the piezoelectric polymer into a voltage that can be effectively conducted by the conducting polymer of the material. Various other industrial applications are possible.

The invention claimed is:

1. An electroactive material comprising:

a piezoelectric polymer substrate comprising fibers made of a piezoelectric polymer, wherein the piezoelectric polymer is poly(vinylidene fluoride) (PVDF); and a conducting polymer coating the fibers of the substrate, the conducting polymer doped with biotin and sodium p-toluenesulfate, wherein the conducting polymer is polypyrrole (PPy).

2. The electroactive material of claim 1, wherein the fibers comprise part of a scaffold.

3. The electroactive material of claim 1, wherein the fibers comprise electrospun fibers.

4. The electroactive material of claim 1, wherein the conducting polymer coating the fibers of the substrate is formed using in situ polymerization.

5. The electroactive material of claim 4, wherein the in situ polymerization comprises electrochemical polymerization.

6. The electroactive material of claim 1, wherein the conducting polymer is loaded with a therapeutic substance.

7. The electroactive material of claim 6, wherein the therapeutic substance is a drug.

8. The electroactive material of claim 6, wherein the therapeutic substance is a growth factor.

9. A method for forming an electroactive material, the method comprising:

forming a substrate by electrospinning fibers of a piezoelectric polymer, wherein the piezoelectric polymer is poly(vinylidene fluoride) (PVDF); and coating the fibers of the substrate with a conducting polymer doped with biotin and sodium p-toluenesulfate by polymerizing the conducting polymer on the fibers in situ using electrochemical polymerization in a solution comprising the biotin, the sodium p-toluenesulfate, and the conducting polymer, wherein the conducting polymer is polypyrrole (PPy).

10. The method of claim 4, further comprising loading the conducting polymer with a therapeutic substance.

11. The method of claim 10, wherein the substance comprises a drug.

12. The method of claim 10, wherein the substance comprises a growth factor.

* * * * *